(12) United States Patent
Nally et al.

(10) Patent No.: US 12,350,102 B2
(45) Date of Patent: Jul. 8, 2025

(54) ULTRASOUND SCANNER WITH DISPLAY INTERFACE

(71) Applicant: FUJIFILM SONOSITE, INC., Bothell, WA (US)

(72) Inventors: Patrick Nally, Seattle, WA (US); Tyler Dawson, Edmonds, WA (US); Kenji Kimura, Seattle, WA (US); John Fogelberg, Seattle, WA (US); Christopher Howard, Seattle, WA (US); Craig Chamberlain, Seattle, WA (US); Andrew Lundberg, Woodinville, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 140 days.

(21) Appl. No.: 18/045,362

(22) Filed: Oct. 10, 2022

(65) Prior Publication Data

US 2024/0115238 A1 Apr. 11, 2024

(51) Int. Cl.
*A61B 8/00* (2006.01)
*A61B 90/98* (2016.01)
*A61B 90/00* (2016.01)

(52) U.S. Cl.
CPC ............ *A61B 8/462* (2013.01); *A61B 8/4263* (2013.01); *A61B 8/4411* (2013.01); *A61B 8/4438* (2013.01); *A61B 8/4472* (2013.01); *A61B 8/4488* (2013.01); *A61B 8/56* (2013.01); *A61B 90/98* (2016.02); *A61B 2090/3904* (2016.02); *A61B 2090/3945* (2016.02)

(58) Field of Classification Search
CPC ..... A61B 8/462; A61B 8/4263; A61B 8/4411; A61B 8/4438; A61B 8/4472; A61B 8/4488; A61B 8/56; A61B 90/98; A61B 2090/3904; A61B 2090/3945
See application file for complete search history.

(56) References Cited

U.S. PATENT DOCUMENTS

| | | | |
|---|---|---|---|
| 11,372,093 B2 | 6/2022 | Lundberg et al. | |
| 2016/0256101 A1* | 9/2016 | Aharoni | A61B 5/0086 |
| 2019/0374199 A1* | 12/2019 | Griffith | A61B 8/4427 |
| 2019/0374200 A1* | 12/2019 | Griffith | A61B 8/4427 |
| 2019/0374201 A1* | 12/2019 | Griffith | A61B 8/4427 |
| 2022/0175347 A1* | 6/2022 | Li | A61B 8/4254 |
| 2023/0389893 A1* | 12/2023 | Misener | A61B 8/462 |

* cited by examiner

*Primary Examiner* — Dixomara Vargas
(74) *Attorney, Agent, or Firm* — Womble Bond Dickinson (US) LLP

(57) ABSTRACT

Systems and methods to provide an ultrasound scanner with a display interface are described. An ultrasound system includes an ultrasound scanner having an interface configured to display a visual representation, and a first transceiver configured to communicate over a communication link. The ultrasound system includes a display device having a reader configured to read the visual representation displayed by the ultrasound scanner, and a second transceiver configured to, responsive to the reader reading the visual representation, initiate communication with the first transceiver of the ultrasound scanner over the communication link to pair the ultrasound scanner and the display device.

19 Claims, 19 Drawing Sheets

120

| Display a visual representation on an interface of an ultrasound scanner having a first transceiver configured to communicate over a communication link | 121 |

| Read, using a reader of a display device, the visual representation, the display device having a second transceiver | 122 |

| Initiate, using the second transceiver, a communication with the first transceiver of the ultrasound scanner over the communication link to pair the ultrasound scanner and the display device | 123 |

| Emit light using at least one light source of an ultrasound scanner having a processor configured to encode data into the light | 131 |

| Receive the light by a receiver of a display device, the display device having a decoder configured to decode the data from the light | 133 |

```
┌─────────────────────────────────────────────────────────────────────────┐
│ Display a pattern on a display interface of an ultrasound scanner having a transceiver, │
│ the display interface including an array of light emitting diodes (LEDs) that are visibly │
│    hidden from an environment outside the ultrasound scanner when the LEDs are          │ — 211
│       inactive, the display interface being sealed from the environment                 │
└─────────────────────────────────────────────────────────────────────────┘
                                        │
┌─────────────────────────────────────────────────────────────────────────┐
│ Communicate, using the transceiver, with a display device over a communication link │
│  based on at least one of a pattern displayed in the display interface according to light │
│         emitted by the LEDs and a property of the light emitted by the LEDs            │ — 213
└─────────────────────────────────────────────────────────────────────────┘
```

FIG. 2B

ULTRASOUND SCANNER WITH DISPLAY INTERFACE

Embodiments disclosed herein relate to ultrasound systems. More specifically, embodiments disclosed herein relate to an ultrasound scanner with a display interface.

BACKGROUND

Generally, wireless transducers help to democratize point of care imaging and empower medical professionals. However, with the emergence of wireless ultrasound transducers also comes new challenges to the user. For example, ultrasound examinations are already a cognitively complex task, requiring the user to properly place an ultrasound probe (e.g., scanner) on the patient while looking away to a separate monitor to view the imaged anatomy. Users often already have both hands occupied and rely on assistants to control the visualization tools on the monitor. Traditional wired transducers are designed to be plugged in and ready to go, with minimal interaction and no interface. Handheld, portable scanners, however, typically do not emulate the simplicity of traditional scanners.

Conventional handheld, wireless ultrasound scanners usually have a simplified interface on the scanner that usually includes a single light emitting diode (LED) or a small group of LEDs to communicate various complex system states (booting up, battery level, system update, etc.) to users. Typically, these system states are displayed through specific patterns of LED behaviors, such as blinking, flashing, or changing colors. These LED behaviors can be quite ambiguous and uninterpretable, especially without any dedicated display. Users are forced to memorize various LED patterns which can be cognitively overloading in a stressful environment. Excess cognitive load can lead to user errors, potentially delay procedures, and result in less than optimum patient care.

In some cases, handheld transducers include a small display screen. These display screens, however, are merely limited to the display of small amounts of data that are usually indicated on the clinical display on an ultrasound machine, and do not facilitate additional use of the transducer beyond that of a conventional ultrasound system.

SUMMARY

Systems and methods to provide an ultrasound scanner with a display interface are described. In some embodiments, an ultrasound system includes an ultrasound scanner having an interface configured to display a visual representation, and a first transceiver configured to communicate over a communication link. The ultrasound system also includes a display device having a reader configured to read the visual representation displayed by the ultrasound scanner, and a second transceiver configured to, responsive to the reader reading the visual representation, initiate communication with the first transceiver of the ultrasound scanner over the communication link to pair the ultrasound scanner and the display device.

In some embodiments, an ultrasound system includes an ultrasound scanner having at least one light source configured to emit light and a processor configured to encode data into the light. The ultrasound system also includes a display device having a receiver configured to receive the light and a decoder configured to decode the data from the light.

In some embodiments, an ultrasound scanner includes a display interface including an array of light emitting diodes (LEDs) that are visibly hidden from an environment outside the ultrasound scanner when the LEDs are inactive, and the display interface is sealed from the environment. The ultrasound scanner also includes a transceiver configured to communicate with a display device over a communication link based on at least one of a pattern displayed in the display interface according to light emitted by the LEDs and a property of the light emitted by the LEDs.

Other systems, machines, and methods to provide an ultrasound scanner with a display interface are also described.

BRIEF DESCRIPTION OF THE DRAWINGS

The appended drawings illustrate examples and are, therefore, exemplary embodiments and not considered to be limiting in scope.

FIG. 1B is a data flow diagram of a process implemented by an ultrasound system according to some embodiments.

FIG. 1C is a data flow diagram of a process implemented by an ultrasound system according to some embodiments.

FIG. 2B is a data flow diagram of a process implemented by an ultrasound scanner according to some embodiments.

DETAILED DESCRIPTION

Systems and methods to provide an ultrasound scanner with a display interface are described. In some embodiments, an ultrasound system includes an ultrasound scanner having an interface configured to display a visual representation and a transceiver configured to communicate over a communication link. The communication link can be wireless, wired, or a combination thereof. The ultrasound system also includes a display device having a reader configured to read the visual representation displayed by the ultrasound scanner, and a second transceiver configured to, responsive to the reader reading the visual representation, initiate communication with the transceiver of the ultrasound scanner over the communication link to pair the ultrasound scanner and the display device.

Embodiments described herein are directed to ultrasound systems that include an ultrasound scanner having an interface that is displayed on the ultrasound scanner using a light source to communicate with a display device (e.g., a tablet, a smart phone, an ultrasound machine, and the like). In some embodiments, a display of the ultrasound scanner (e.g., an LED grid array) is used to communicate system states and streamline workflow, including interaction of the ultrasound scanner with a display device (e.g., tablet, smart phone, ultrasound machine, and the like), in ways that are not possible with conventional ultrasound systems.

Reference in the specification to "one embodiment", "an embodiment", "one example", or "an example" means that a particular feature, structure, or characteristic described in conjunction with the embodiment can be included in at least one embodiment. The appearances of the phrases "in one embodiment" or "in an embodiment" in various places in the specification do not necessarily all refer to the same embodiment. The processes depicted in the figures that follow are performed by processing logic that comprises hardware (e.g., circuitry, dedicated logic, etc.), software, firmware, or combinations thereof. Although the processes are described below in terms of some sequential operations, it should be appreciated that some of the operations described may be performed in a different order. Moreover, some operations may be performed in parallel rather than sequentially. Furthermore, it should be appreciated that not all operations of the processes described necessarily need to be performed.

In the specification, the term "and/or" describes three relationships between objects that may exist. For example, A and/or B may represent the following cases: only A exists, both A and B exist, and only B exist, where A and B may be singular or plural.

Figure 1A:
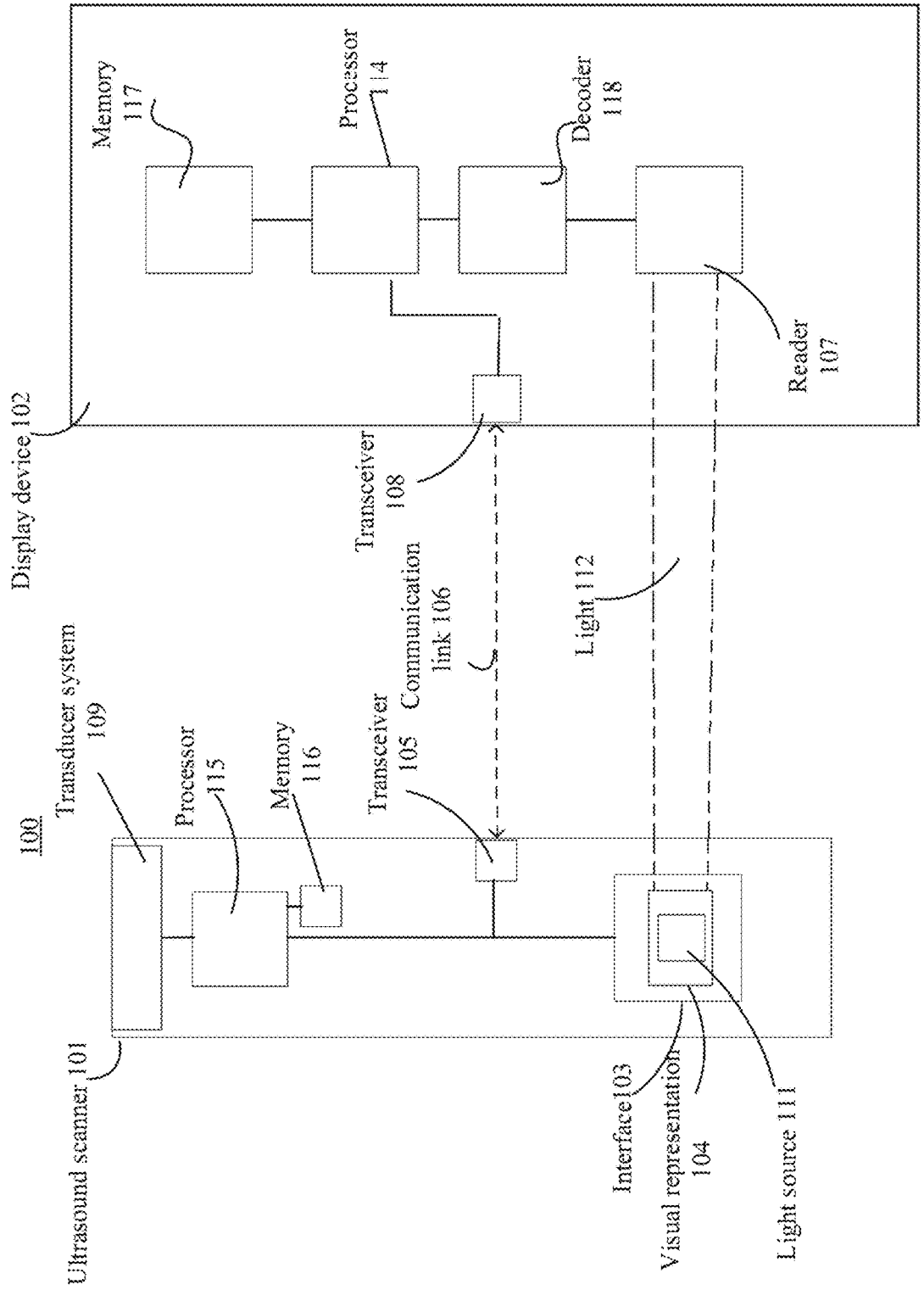
FIG. 1A is a view illustrating an ultrasound system according to some embodiments.

FIG. 1A is a view 100 illustrating an ultrasound system 100 according to some embodiments. As shown in FIG. 1A the ultrasound system 100 includes an ultrasound scanner 101 and a display device 102. In some embodiments, the ultrasound scanner 101 is a wireless scanner (e.g., a wireless probe). In some embodiments, the ultrasound scanner is a wired scanner (e.g., a probe configured to be connected via a cable to the display device 102). The ultrasound scanner 101 includes an interface 103 that is configured to display a visual representation 104. In some embodiments, the visual representation includes a quick response (QR) code, a bar code, an animation sequence, or any combination thereof. In some embodiments, the interface 103 is sealed from an environment outside the ultrasound scanner. In some embodiments, the interface 103 includes an array of light emitting diodes (LEDs) that are visibly hidden from the environment when the LEDs are inactive, as described in further detail below.

As shown in FIG. 1A, the ultrasound scanner 101 includes a transceiver 105 that is configured to communicate over a communication link 106, such as a Wi-Fi network, near-near field communication link, cable, or combinations thereof.

The ultrasound scanner 101 includes a transducer system 109 that generates ultrasound data based on reflections of ultrasound signals transmitted by the transducer system. As shown in FIG. 1A, a processor 115 is coupled to the transducer system 109 and a memory 116 is coupled to the processor 115 to store executable instructions to perform the methods described herein. In some embodiments, memory 116 includes one or more memories. In some embodiments, processor 115 includes one or more processors.

As shown in FIG. 1A, the display device 102 includes a reader 107 that is configured to read the visual representation 104 displayed by the ultrasound scanner 101. The display device 102 includes a transceiver 108 that is configured to, responsive to the reader 107 reading the visual representation 104, initiate communication with the transceiver 105 over the communication link 106 to pair the ultrasound scanner 101 and the display device 102. The communication link 106 can be wireless, wired, or a combination thereof. In some embodiments, the visual representation 104 includes a pattern, an icon, an animation sequence, other visual representation, or any combination thereof that is displayed in the display interface 103 according to light emitted by the LEDs and a property of the light emitted by the LEDs, as described in further detail below.

FIG. 1B is a data flow diagram of a process 120 implemented by an ultrasound system according to some embodiments. The process 120 can be performed by processing logic that can comprise hardware (circuitry, dedicated logic, etc.), software (such as is run on a general-purpose computer system or a dedicated machine), firmware, or combinations thereof. As shown in FIG. 1B, process 120 includes processing logic displaying a visual representation on an interface of an ultrasound scanner having a first transceiver configured to communicate over a communication link at block 121. The communication link can be wireless, wired, or a combination thereof. Process 120 continues at block 122 that involves processing logic reading, using a reader of a display device, the visual representation displayed by the ultrasound scanner, the display device having a second transceiver. At block 123, responsive to the reader reading the visual representation, processing logic initiates, using the second transceiver of the display device, a communication with the first transceiver of the ultrasound scanner over the communication link to pair the ultrasound scanner and the display device.

Returning to FIG. 1A, in some embodiments, the ultrasound scanner 101 includes at least one light source 111 to emit light 112. For instance, the light source can be included as part of the interface 103, such as including one or more LEDs of the interface 103. Additionally or alternatively, the light source can be separate from the interface 103. In some embodiments, the light 112 includes visible light having a wavelength between 380 nanometers and 740 nanometers, or other wavelength.

In some embodiments, the processor 115 is configured to encode data into the light 112. In some embodiments, the data encoded into the light indicates at least one of an availability, a battery status, a cleanliness status, and a transducer configuration of the ultrasound scanner 101.

In some embodiments, the reader 107 includes a receiver including one or more sensors configured to receive and sense the light 112. The display device 102 includes a processor 114 and a memory 117 coupled to the processor 114 to store executable instructions to perform the methods described herein. The display device 102 includes a decoder 118 that is coupled to the processor 114 and is configured to decode the data from the light 112 that is received and sensed by the reader 107.

FIG. 1C is a data flow diagram of a process 130 implemented by an ultrasound system according to some embodiments. The process 130 can be performed by processing logic that can comprise hardware (circuitry, dedicated logic, etc.), software (such as is run on a general-purpose computer system or a dedicated machine), firmware, or combinations thereof. As shown in FIG. 1C, process 130 includes emitting light using at least one light source of an ultrasound scanner having a processor configured to encode data into the light at block 131. At block 133 the light is received by a receiver of a display device, the display device having a decoder configured to decode the data from the light.

Returning to FIG. 1A, in some embodiments, the transceiver 108 is implemented to initiate communication with the transceiver 105 over the communication link 106 based on the data decoded from the light, to pair the ultrasound scanner 101 and the display device 102.

In some embodiments, the processor 115 is implemented to encode the data into the light 112 by modulating at least one of a frequency of the light, a phase of the light, an amplitude of the light, and a polarization of the light. In some embodiments, the at least one light source 111 includes multiple light sources. In some embodiments, the processor 115 is implemented to encode the data into the light based on locations of the multiple light sources on the ultrasound scanner, as described in further detail below.

In some embodiments, the ultrasound scanner 101 is implemented to communicate with an additional ultrasound scanner over an additional communication link (e.g., a wireless communication link) to indicate that the ultrasound scanner is in the communication with the display device 102 and not available for pairing with the additional ultrasound scanner. The additional ultrasound scanner and the additional communication link are not shown in FIG. 1A for clarity.

In some embodiments, the ultrasound scanner 101 includes a light source (such as the light source 111) that is configured to project light onto a patient to indicate an insertion point for an interventional instrument. In some embodiments, the light source is configured to project the light onto the patient to indicate a shape of a blood vessel, as described in further detail below. In some embodiments, the light source of the ultrasound scanner includes light emitting diodes (LEDs) of the display interface 103, and the light source is implemented to generate the light by beamforming the LEDs, as described in further detail below. In some embodiments, the light source includes a mini projector. Additionally or alternatively, the light source can include a micro-electro-mechanical system (MEMS) device.

In some embodiments, the transducer system 109 is implemented to generate ultrasound data based on reflections of ultrasound signals transmitted by the transducer system at a patient-worn identifier and the processor 115 is implemented to determine patient identification data based on the ultrasound data. In some embodiments, the interface 103 and/or the display device 102 is implemented to display the patient identification data, as described in further detail below.

In some embodiments, the ultrasound scanner 101 is configured to obtain an instruction to move the ultrasound scanner 101, and the interface 103 is configured to display an additional visual representation (not shown in FIG. 1A) that indicates how to move the ultrasound scanner based on the instruction. In some embodiments, the ultrasound scanner 101 is configured to receive a removable head having a transducer array, and the interface 103 is configured to display an identifier of the removable head. In some embodiments, the identifier indicates that the transducer array is one of linear, planar, phased, and curved, as described in further detail below.

In some embodiments, the at least one light source 111 includes multiple light sources. In some embodiments, the ultrasound system 100 includes a registration system that includes one or more light sensors implemented to sense the light emitted from the multiple light sources and a processor system that is implemented to determine an orientation of the ultrasound scanner 101 based on the light sensed by the one or more light sensors. In some embodiments, the one or more light sensors are part of the reader 107 and processor system 114 is implemented to determine an orientation of the ultrasound scanner 101 based on the light sensed by the one or more light sensors. Additionally or alternatively, the one or more light sensors can be separate from the display device 102.

In some embodiments, transceiver 105 is configured to communicate with the display device 102 over the communication link 106 based on at least one of a pattern displayed by the display interface 103 according to light emitted by the LEDs and a property of the light emitted by the LEDs of the light source 111, as described in further detail below.

Figure 1D:
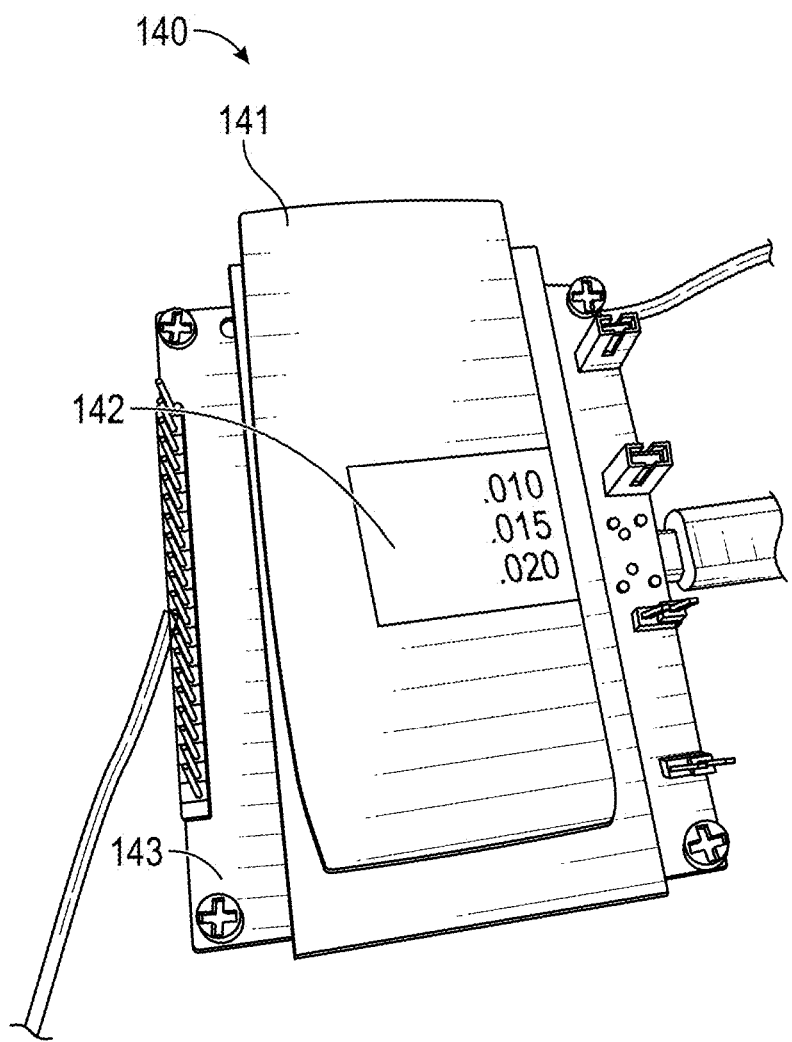
FIG. 1D is a view illustrating an ultrasound scanner interface according to some embodiments.

FIG. 1D is a view 140 illustrating an ultrasound scanner interface 141 according to some embodiments. In some embodiments, the ultrasound scanner interface 141 represents one of the scanner interfaces described in the application. As shown in FIG. 1D, the ultrasound scanner interface 141 includes a dot matrix 142 including m×n LEDs that are spaced a distance (e.g., 2 millimeters (mm) or other distance) apart and paired with a microcontroller 143. In some embodiments, m and n can be any number greater than zero. In some embodiments, the dot matrix 142 is a rectangular, circular, square or other shape dot matrix. In some embodiments, the dot matrix 142 is a 5×20 LED rectangular dot matrix having the LEDs that are spaced about 2 mm apart and paired with the microcontroller. In some embodiments, the LED grid array enables the scanner to be far more descriptive when communicating specific system states including but not limited to, battery status, Bluetooth pairing, warnings, etc. than conventional scanners. For example, instead of having to remember a sequence of flashes from a single LED to indicate a system update, the LED matrix could simply spell "updating" or perhaps display an icon that is easier to interpret. The LED array allows the scanner to communicate a large number of behaviors, along with the ability to update new behaviors, all while reducing cognitive load. For example, a new or updated behavior can be included in a software update to the scanner, so that the LEDs can be re-programmed to display a new pattern, icon, animation sequence, etc., to update an existing behavior or add a new behavior to the scanner.

Figure 2A:
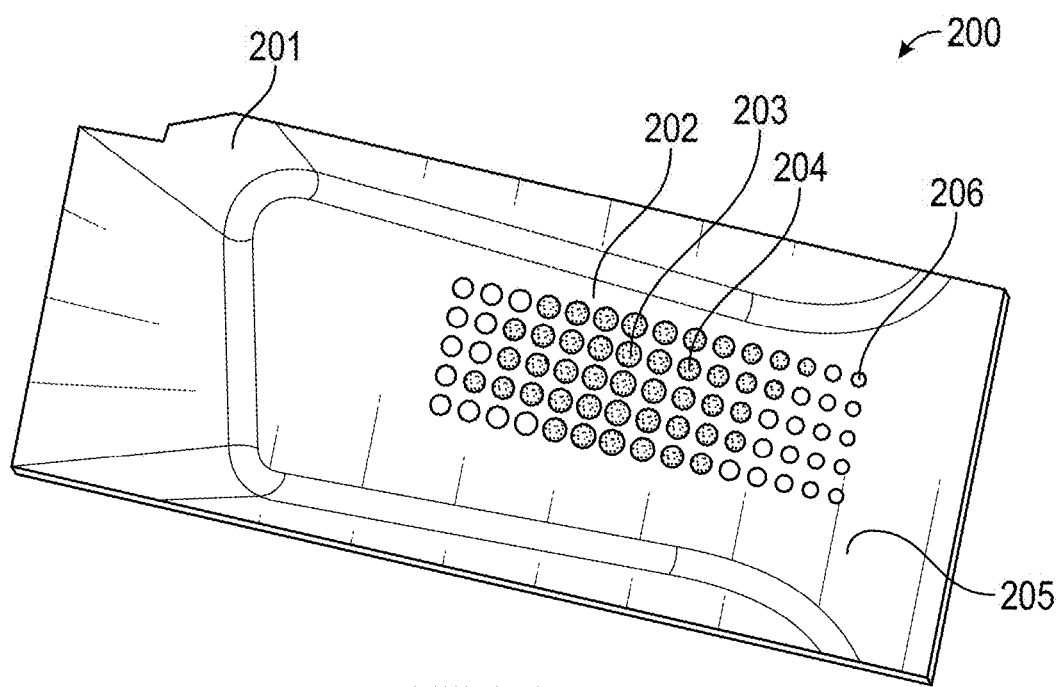
FIG. 2A is a view illustrating an array housing enclosure of an ultrasound scanner according to some embodiments.

FIG. 2 is a view 200 illustrating an array housing enclosure of an ultrasound scanner 201 with a display interface 202 according to some embodiments. In some embodiments, ultrasound scanner 201 represents one of the ultrasound scanners described in the application. As shown in FIG. 2, the display interface 202 includes an array of LEDs that produce a plurality of pixels, such as an LED that generates a pixel 203, an LED that generates a pixel 204 and an LED that generates a pixel 206. As shown in FIG. 2, the LEDs of the grid array are visibly hidden from an environment outside the ultrasound scanner 201 when the LEDs are inactive. As shown in FIG. 2, the LEDs of the display interface 201 are sealed from the outside environment of the scanner by an array housing enclosure 205.

As shown in FIG. 2, the LED grid is a "deadfronted" system meaning that the LEDs are only visible when the LEDs are turned on. The "deadfronting" can be achieved by placing the LED array behind array housing enclosure 205. In some embodiments, the array housing enclosure 205 is a molded plastic housing enclosure. In some embodiments, the back side of the array housing enclosure 205 has pockets (e.g., openings 302 shown in FIG. 3) for placing individual LEDs. The LEDs of the array are placed in the individual pockets to transmit the light through the front side of the array housing enclosure 205. Each LED of the array produces an individual pixel, such as a pixel 203 having a predetermined size that does not mix with one another. In some embodiments, the individual openings 302 formed in the back side 301 of the array housing have a predetermined depth so that the light transmitted by the LED is collimated and not mixed with the light generated by other LEDs of the array. In some embodiments, the LED grid array has a single color (e.g., blue, white, or green). In alternative embodiments, the LED grid array has multiple colors.

FIG. 2B is a data flow diagram of a process 210 implemented by an ultrasound scanner according to some embodiments. The process 210 can be performed by processing logic that can comprise hardware (circuitry, dedicated logic, etc.), software (such as is run on a general-purpose computer system or a dedicated machine), firmware, or combinations thereof. As shown in FIG. 2B, process 210 includes displaying a pattern on a display interface of an ultrasound scanner having a transceiver, the display interface of the ultrasound scanner including an array of light emitting diodes (LEDs) that are visibly hidden from an environment outside the ultrasound scanner when the LEDs are inactive, the display interface being sealed from the environment, at block 211. At block 122 the transceiver communicates with a display device over a communication link (e.g., a wireless communication link or a wired communication link) based on at least one of a pattern displayed in the display interface according to light emitted by the LEDs and a property of the light emitted by the LEDs.

Figure 3:
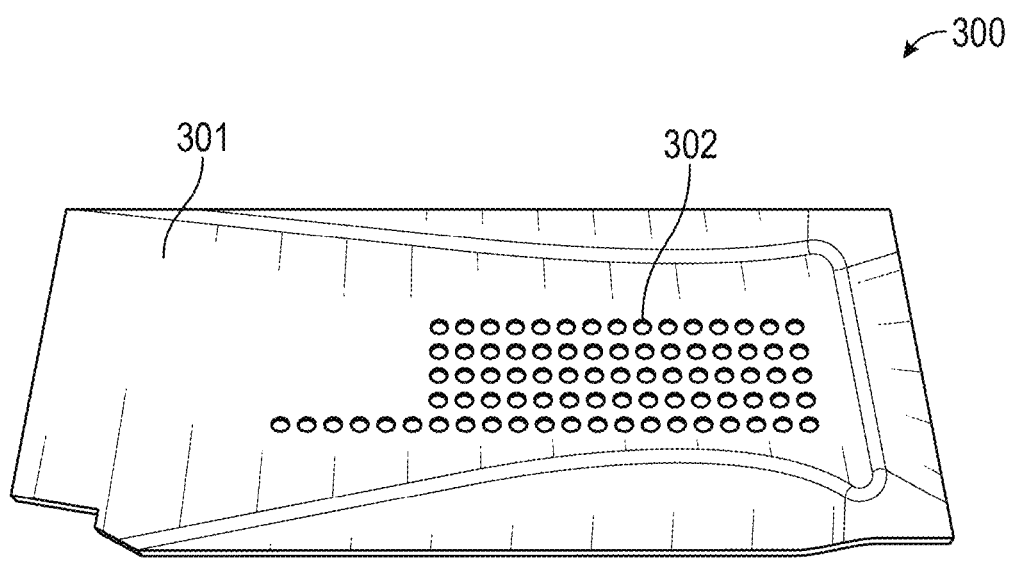
FIG. 3 is a view illustrating an array housing enclosure of the ultrasound scanner according to some embodiments.

FIG. 3 is a view 300 illustrating an array housing enclosure 301 of the ultrasound scanner according to some embodiments. In some embodiments, array housing enclosure 301 represents one of the array housing enclosures described in the application. As shown in FIG. 3 the back side of the array housing enclosure 301 has locally machined thinned openings, such as an opening 302 to place individual LEDs and allow light from an LED of the LED array to pass through the front side of the array housing disclosure, as illustrated in FIG. 2. The "deadfronted" assembly of the LED array provides a smooth surface of the scanner, uses less parts and enables easier cleanability by removing unwanted parting lines than conventional systems. The "deadfronted" LED array provides the interface that is visibly hidden from an environment when the LEDs are not active, so that distraction of a user during ultrasound examination is avoided.

Figure 4:
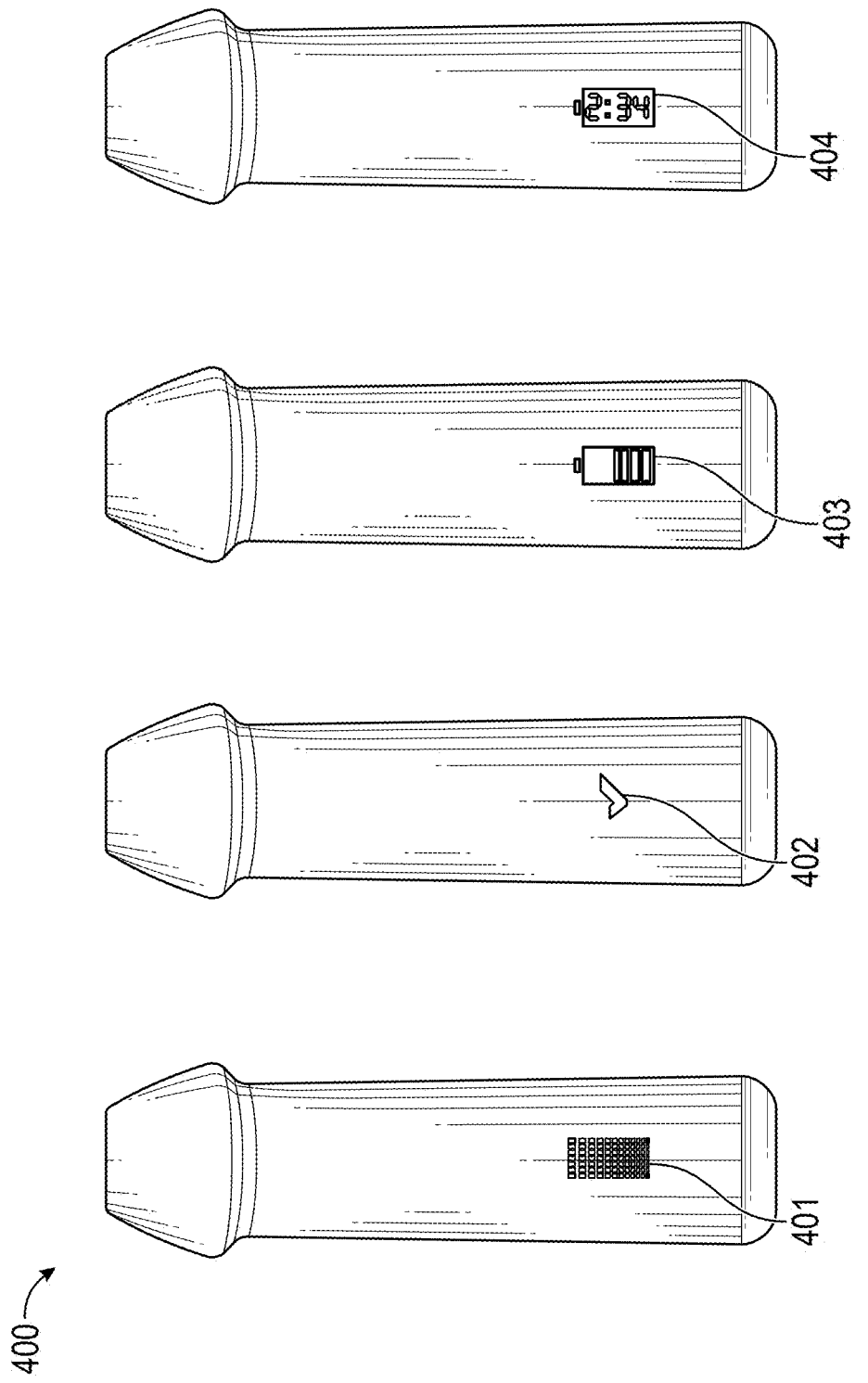
FIG. 4 is a view illustrating examples of information displayed with an LED array on an ultrasound scanner according to some embodiments.

FIG. 4 is a view 400 illustrating examples of information displayed with an LED array on an ultrasound scanner according to some embodiments. Each individual LED in the array can be turned on/off, dimmed, or programmed for animation, so that the visual representation displayed on the display interface of the scanner can change. In some embodiments, the LEDs can be programmed via a software update to display updated or new patterns, e.g., patterns 401, 402, 403 and 404 on the ultrasound scanner interface.

Pairing Scanner with Display Device

In one example, the scanner includes a display interface, such as an LED matrix or array as described above, or any suitable display, such as an LCD, OLED, etc. The display can be of any suitable shape, size, and dimension. For instance, the display can be a 2D display or a 3D display that can display any suitable visual representation that can be used to initiate pairing with a display device, such as a tablet, smart phone, ultrasound machine, heads-up display, smart glasses/goggles, and the like. For example, the display interface of the scanner can display a visual representation, such as a bar code (one dimensional or two dimensional), a quick response (QR) code, a glyph, an optical character, a sequence (e.g., an animation sequence), etc. In an example, the scanner is configured to display the visual representation on the display interface upon powering on the scanner, so that no explicit user selection of the visual representation is needed. The display device can include a reader configured to read the visual representation.

Once the display device reads the visual representation, the display device can initiate communication with the scanner over a wireless communication link, automatically and without additional user intervention, to pair the scanner and the display device. By using the display interface of the scanner to pair the scanner with the display device, the user does not need to perform the steps of navigating a menu on the display device, selecting the scanner, and manually enabling pairing. Rather, the user may select to display the visual representation on the display interface of the scanner, move the scanner in view of the reader of the display device, and initiate pairing without further user input. Hence, the patient can receive care more quickly than with conventional wireless scanners that require manual interaction and selection via the display device to initiate the pairing.

Figure 5A:
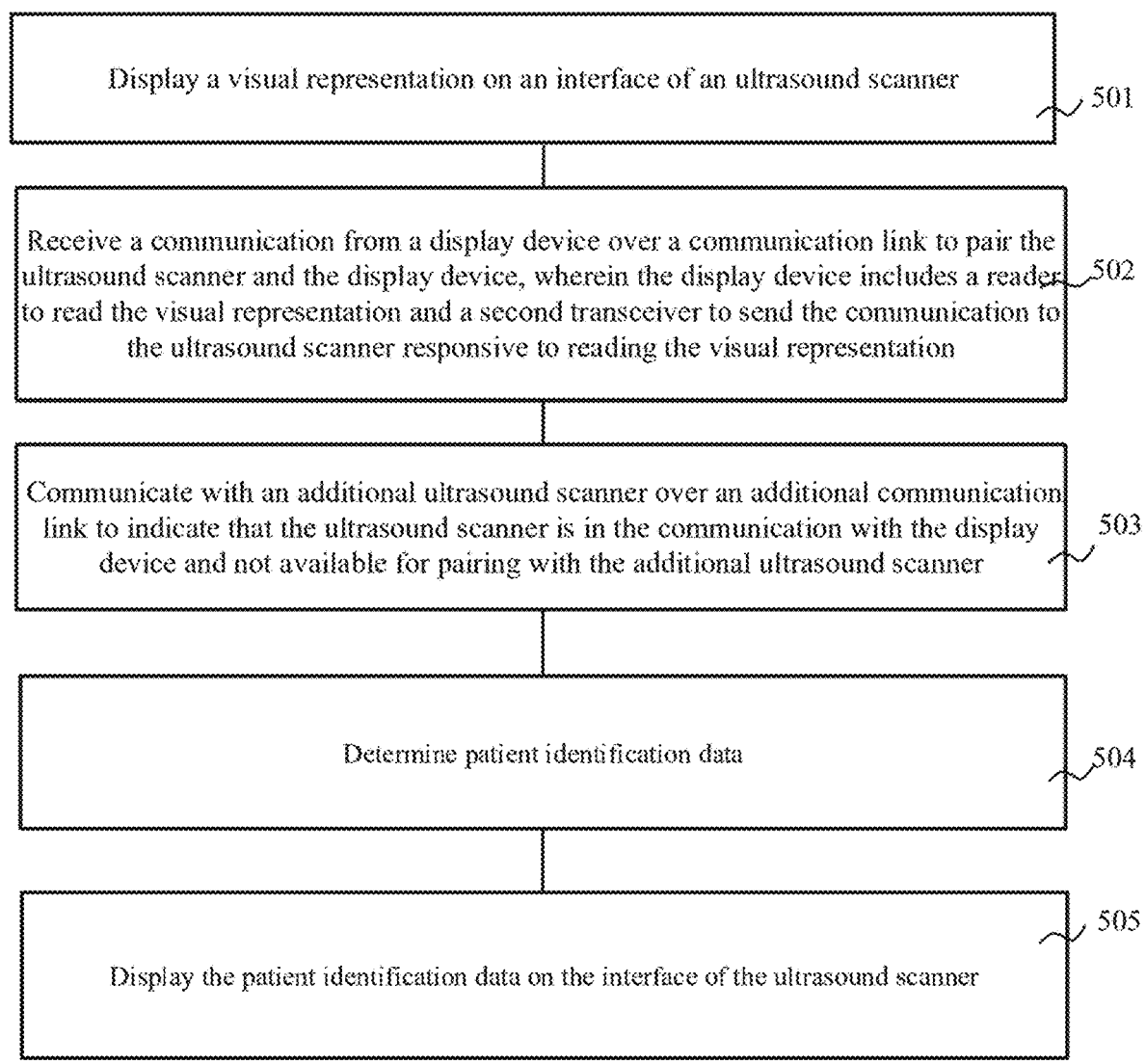
FIG. 5A is a data flow diagram of a process implemented by an ultrasound scanner to perform pairing with a display device according to some embodiments.

FIG. 5A is a data flow diagram of a process 500 implemented by an ultrasound scanner to perform pairing with a display device according to some embodiments. The process can be performed by processing logic that can comprise hardware (circuitry, dedicated logic, etc.), software (such as is run on a general-purpose computer system or a dedicated machine), firmware, or combinations thereof. In some embodiments, the ultrasound scanner includes a transducer system that generates, as part of an ultrasound examination, ultrasound data based on reflections of ultrasound signals transmitted by the transducer system, a transceiver implemented at least partially in hardware of the ultrasound scanner that communicates, over a communication link, the ultrasound data to a display device that displays an ultrasound image based on the ultrasound data, as described above. In an example, the communication link includes a wireless communication link. In some embodiments, the ultrasound scanner includes one or more processors and a memory coupled to the processor(s) to perform the process 500.

Referring to FIG. 5A, process 500 includes processing logic displaying a visual representation on an interface of an ultrasound scanner at block 501. In some embodiments, the visual representation includes at least one of a quick response (QR) code, a bar code, and an animation sequence. Process 500 continues at block 502 that involves processing logic receiving a communication from a display device over a communication link to pair the ultrasound scanner and the display device. In an example, the communication link includes a wireless communication link. In some embodiments, the display device includes a reader to read the visual representation displayed on the ultrasound scanner interface and a transceiver to send the communication to the ultrasound scanner responsive to reading the visual representation. In some embodiments, the display device is a tablet, a smart phone, an ultrasound machine, and the like. At block 503, processing logic communicates with an additional ultrasound scanner over an additional wireless communication link to indicate that the ultrasound scanner is in the communication with the display device so that the display device is not available for pairing with the additional ultrasound scanner.

At block 504, processing logic determines patient identification data. In some embodiments, the ultrasound scanner includes a transducer system that is implemented to generate ultrasound data based on reflections of ultrasound signals transmitted by the transducer system at a patient-worn identifier and processing logic determines patient identification data based on the ultrasound data.

At block 505 processing logic displays the patient identification data on the interface of the ultrasound scanner. In some embodiments, processing logic of the ultrasound scanner obtains an instruction to move the ultrasound scanner, and displays, on the interface, an additional visual representation that indicates how to move the ultrasound scanner based on the instruction. In some embodiments, processing logic of the ultrasound scanner receives a removable head having a transducer array, and displays an identifier of the removable head on the interface. In some embodiments, the identifier of the removable head indicates the transducer array of the removable head as one of linear, planar, phased, and curved.

In some embodiments, the ultrasound scanner includes a light source configured to project light onto a patient to indicate an insertion point for an interventional instrument. In some embodiments, the light source of the ultrasound scanner projects the light onto the patient to indicate a shape of a blood vessel. In some embodiments, the light source of the ultrasound scanner includes light emitting diodes (LEDs) of the display, and the light source is implemented to generate the light by beamforming the LEDs. Additionally or alternatively, the light source can include a mini projector or MEMS device to generate the light, including to beamform the light generated by the mini projector or MEMS device.

Figure 5B:
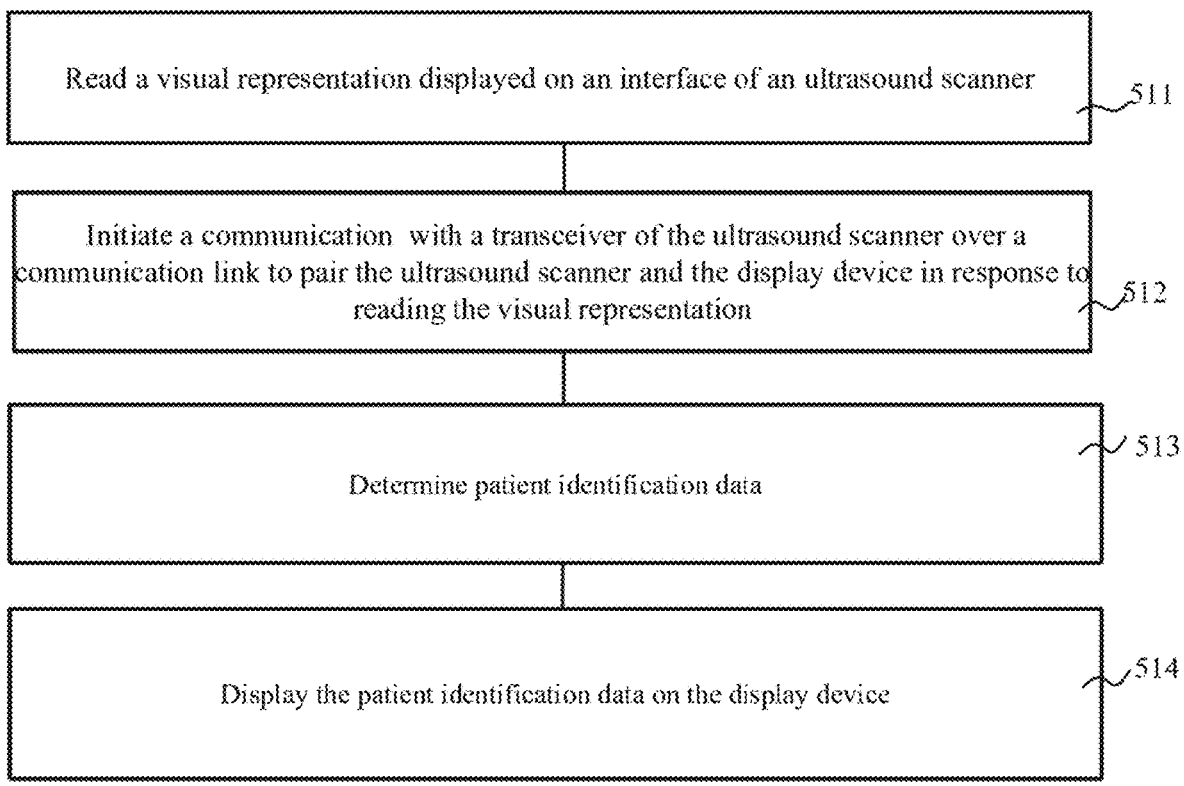
FIG. 5B is a data flow diagram of a process implemented by a display device to perform pairing with an ultrasound scanner according to some embodiments.

FIG. 5B is a data flow diagram of a process 510 implemented by a display device to perform pairing with an ultrasound scanner according to some embodiments. The process can be performed by processing logic that can comprise hardware (circuitry, dedicated logic, etc.), software (such as is run on a general-purpose computer system or a dedicated machine), firmware, or combinations thereof. In some embodiments, the display device includes a reader including one or more light sensors that reads a visual representation displayed on an interface of an ultrasound scanner and a transceiver that is implemented at least partially in hardware of the display device. In some embodiments, the transceiver of the display device receives the ultrasound data from the transceiver of the ultrasound scanner over the wireless communication link, and processing logic displays an ultrasound image based on the ultrasound data on the display device. In some embodiments, the ultrasound scanner display device includes one or more processors and a memory coupled to the processor(s) to perform the process 510.

Referring to FIG. 5B, process 510 includes processing logic reading, by a reader, a visual representation displayed on an interface of an ultrasound scanner (block 511). At block 512 processing logic initiates a communication with a transceiver of the ultrasound scanner over a wireless communication link to pair the ultrasound scanner and the display device in response to reading the visual representation. At block 513 processing logic determines patient identification data. At block 514 processing logic displays the patient identification data on the display device, as described in further detail below.

In an example, the ultrasound scanner can include any suitable number of light sources. For instance, the light sources, such as LEDs and/or MEMS lasers, can be included on substantially the entire surface of the scanner, or within a grid array making up a display interface, as described above. In some embodiments, the display interface of the ultrasound scanner has a rectangular, circular, square or other shape. Hence, the light sources can be part of the display interface of the scanner, or separate therefrom. The scanner can encode data into a property of light emitted by the light sources, and communicate the data to a display device. The scanner can encode the data in any suitable way, such as by modulating a phase, frequency, polarization, amplitude, pulse rate, etc. of the light. Similar to the visual representation (e.g., a QR code) displayed by the scanner's display interface as described above, the data encoded into the light can be read by the display device and used for pairing the scanner with the display device. Additionally or alternatively, the data can be used for communicating a status of the scanner to the display device, e.g., a scanner availability, a battery/charge status, a state of cleanliness, the type of transducer in the scanner, etc. For example, the scanners can be housed in an ultrasound cart, battery charger, etc., and a user can swipe a display device across the scanners. The display device can then display the status data for each of the scanners, and the user and/or display device can determine which scanner is suitable to select for an examination.

In an example, an ultrasound system includes an ultrasound scanner having at least one light source configured to emit light and a processor configured to encode data into the light. The ultrasound system also includes a display device having a receiver configured to receive the light and a decoder configured to decode the data from the light. To pair the scanner and the display device, the ultrasound scanner can include a first transceiver configured to communicate over a wireless communication link, and the display device can include a second transceiver configured to communicate over the wireless communication link. Based on the data decoded from the light, the second transceiver can initiate communication with the first transceiver over the wireless communication link to pair the ultrasound scanner and the display device. For instance, the data can include a paring request, pairing parameters, etc.

The processor can encode the data into the light by modulating at least one of a frequency of the light, a phase of the light, an amplitude of the light, and a polarization of the light. In one example, the processor encodes the data by spatially encoding the data, e.g., based on positions of the light sources on the scanner. For instance, the position of the light source on the scanner can serve as the modulation. The light emitted by the light sources can be visible light, e.g., having a wavelength between 380 nanometers and 740 nanometers. Additionally or alternatively, the light can include non-visible light, e.g., outside the visible spectrum, such as infrared (IR).

Figure 6A:
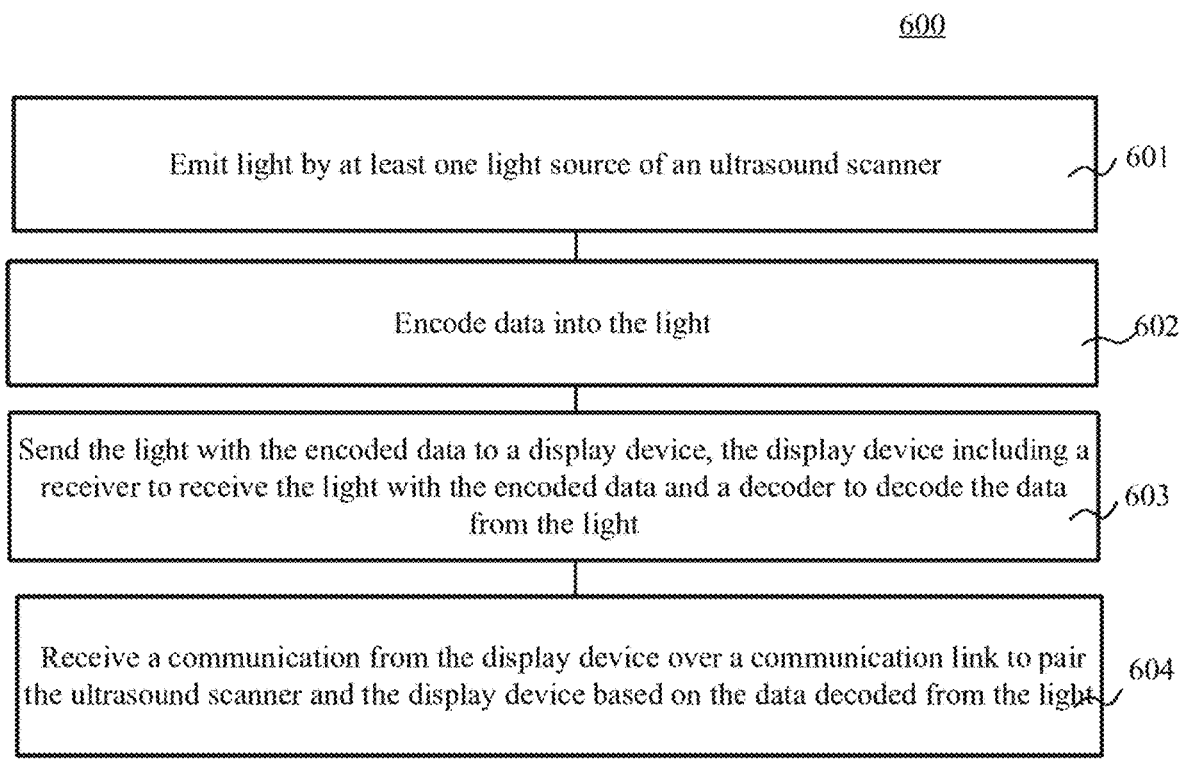
FIG. 6A is a data flow diagram of a process implemented by an ultrasound scanner to perform pairing with a display device according to some embodiments.

FIG. 6A is a data flow diagram of a process 600 implemented by an ultrasound scanner to perform pairing with a display device according to some embodiments. The process can be performed by processing logic that can comprise hardware (circuitry, dedicated logic, etc.), software (such as is run on a general-purpose computer system or a dedicated machine), firmware, or combinations thereof. In some embodiments, the ultrasound scanner includes a transducer system that generates, as part of an ultrasound examination, ultrasound data based on reflections of ultrasound signals transmitted by the transducer system, a transceiver implemented at least partially in hardware of the ultrasound scanner that communicates, over a wireless communication link, the ultrasound data to a display device that displays an ultrasound image based on the ultrasound data, as described above. In some embodiments, the ultrasound scanner includes one or more processors and a memory coupled to the processor(s) to perform the process 600.

Referring to FIG. 6A, process 600 includes processing logic emitting light by using at least one light source of an ultrasound scanner (block 601). In some embodiments, the light includes visible light having a wavelength between 380 nanometers and 740 nanometers. In some embodiments, the at least one light source includes multiple light sources. In some embodiments, an ultrasound system includes a registration system including one or more light sensors and a processor system coupled to the one or more light sensors. In some embodiments, the one or more light sensors sense the light emitted from the multiple light sources and the processor system determines an orientation of the ultrasound scanner based on the light sensed by the one or more light sensors. The orientation can indicate a position of the ultrasound scanner in a coordinate system.

At block 602 processing logic encodes data into the light. In some embodiments, processing logic encodes the data into the light by modulating at least one of a frequency of the light, a phase of the light, an amplitude of the light, and a polarization of the light. In some embodiments, the at least one light source includes multiple light sources, and the processing logic encodes the data into the light based on locations of the multiple light sources on the ultrasound scanner. For instance, light from a first location can indicate a first piece of data (such as a "1"), and light from a second location can indicate a second piece of data (such as a "0"). In some embodiments, the data encoded into the light indicates at least one of an availability, a battery status, a cleanliness status, and a transducer configuration of the ultrasound scanner. At block 603 processing logic sends the light with the encoded data to a display device. In some embodiments, the display device includes a receiver that includes one or more light sensors to receive the light with the encoded data and a decoder to decode the data from the light. At block 604 processing logic receives, by using the transceiver, a communication from the display device over the wireless communication link to pair the ultrasound scanner and the display device based on the data decoded from the light, as described above.

Figure 6B:
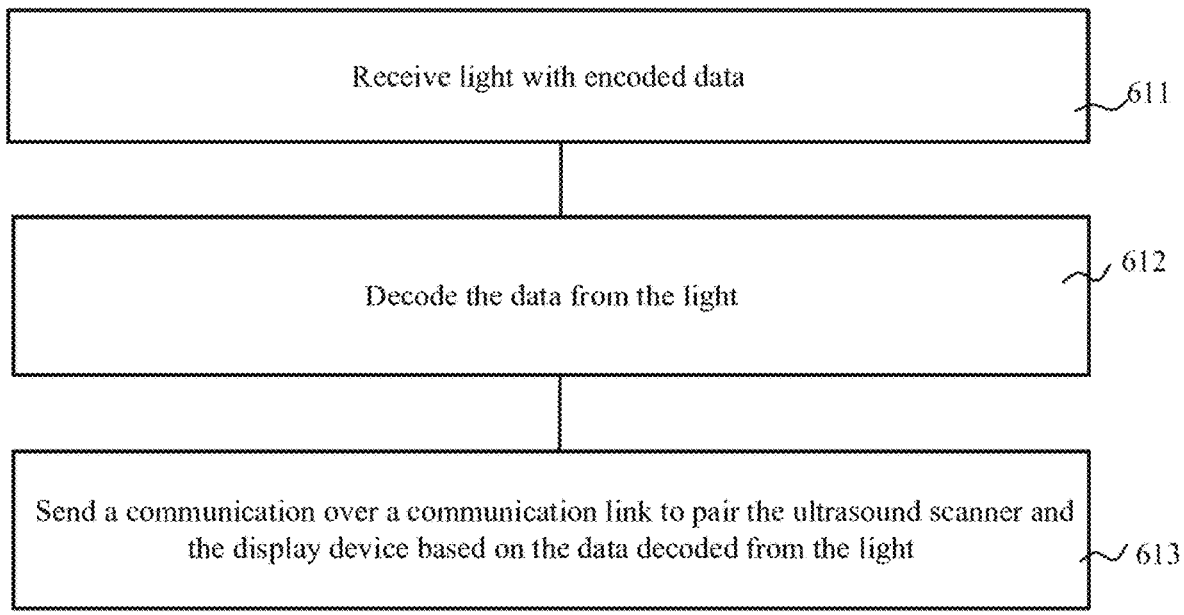
FIG. 6B is a data flow diagram of a process implemented by a display device to perform pairing with an ultrasound scanner according to some embodiments.

FIG. 6B is a data flow diagram of a process 610 implemented by a display device to perform pairing with an ultrasound scanner according to some embodiments. The process can be performed by processing logic that can comprise hardware (circuitry, dedicated logic, etc.), software (such as is run on a general-purpose computer system or a dedicated machine), firmware, or combinations thereof. In some embodiments, the display device includes a reader including one or more light sensors that reads light emitted from at least one light source, such as a visual representation displayed on an interface of an ultrasound scanner, and a transceiver that is implemented at least partially in hardware of the display device. In some embodiments, the transceiver of the display device receives the ultrasound data from the transceiver of the ultrasound scanner over the wireless communication link, and processing logic displays an ultrasound image based on the ultrasound data on the display device. In some embodiments, the display device includes one or more processors and a memory coupled to the processor(s) to perform the process 610.

Referring to FIG. 6B, process 610 includes processing logic receiving, by using a receiver, light with encoded data at block 611. At block 612 processing logic decodes the data from the light. At block 613 processing logic sends a communication over the wireless communication link to pair the ultrasound scanner and the display device based on the data decoded from the light, as described above.

In one example, the display interface of the scanner can be configured as a fingerprint reader, and the fingerprint can be used as part of the pairing process. For instance, a user can place their finger on the display interface and the scanner can authenticate the user (e.g., confirm their identity, access level, job title, combinations thereof, extract a user ID, and the like) based on their fingerprint. As an example, the display interface of the scanner can include a capacitive surface configured to generate a fingerprint image from the user placing their finger on the display interface. The scanner can access a database and match features of the fingerprint image to features of an image in the database to authenticate the user. In some embodiments, the scanner includes the database that stores fingerprint data for authentication. In some embodiments, the database that stores fingerprint data for authentication is remote to the scanner.

The display interface can read a fingerprint as part of pairing the scanner and the display device. For instance, a user can authenticate themselves to a display device, such as by entering a password on the display device, providing biometric input (e.g., fingerprint, eye scan, ear scan, etc.), speech, combinations thereof, and the like. To initiate pairing of the scanner and the display device, the user can then place their finger on the display interface of the scanner that is configured as a fingerprint reader. The scanner can authenticate the user via the fingerprint, and search for an available display device that has also been authenticated by the user, e.g., by transmitting pairing queries that include or indicate a user ID. When a display device that has been authenticated by the user receives the pairing query from the scanner, the scanner and the display device can initiate pairing. In an example, initiating the pairing includes verifying knowledge of the user ID, without communicating the user ID. For instance, the scanner and/or display device can communicate data that shows it is in possession of the user ID without exposing the user ID itself.

In one example, the scanner includes one or more light sources and light sensors on the head of the scanner, e.g., on the lens cover through which ultrasound is transmitted and received by the scanner. The scanner can configure the light sources to emit light and the light sensors to measure a property of the emitted light and/or light reflected from the patient. Based on light measured by the light sensors, a biometric property of the patient can be determined by the ultrasound system, including a pulse oximetry, surface blood parameters, peripheral blood flow on the skin, and the like.

In an example, the ultrasound system includes a registration system to determine an orientation of the ultrasound scanner, such as coordinates to represent six degrees of freedom (6DOF), yaw, pitch, and roll angles, etc. Typically, 6DOF refers to the freedom of movement of a body in three-dimensional space. For example, the body is free to change position as forward/backward (surge), up/down (heave), left/right (sway) translation in three perpendicular axes, combined with changes in orientation through rotation about three perpendicular axes, often termed yaw (normal axis), pitch (transverse axis), and roll (longitudinal axis). The registration system can be implemented on the display device, or in a separate device that is in view of the scanner, or combinations thereof.

The registration system can include one or more light sensors (e.g., cameras, IR sensors, etc.) to sense the light emitted from the light sources on the scanner. The registration system can also include a processor system to determine an orientation of the ultrasound scanner based on the light sensed by the one or more light sensors. For instance, the processor system can implement any suitable algorithm that receives light received by the sensors, or properties of the received light, to determine an orientation of the scanner. The processor can have knowledge of the shape of the scanner and locations of the light sources on the scanner. In an example, the registration system determines an orientation of the ultrasound scanner based on light received from a display interface of the scanner, e.g., based on a pattern displayed on the display interface. For instance, the registration system can compare the shape of a known pattern displayed on the display interface of a scanner when looking straight at the display interface to the shape of a reconstructed pattern generated by the light received by the light sensors of the registration system. Based on the differences of the known pattern and the reconstructed pattern, the registration system can determine the orientation of the scanner. Based on the determined orientation of the scanner, the processor can generate an avatar of the scanner for placement in an augmented reality (AR) and/or virtual reality (VR) environment. This way, a remote user can look at the avatar of the scanner to determine a current position of the scanner for telemedicine applications.

Figure 7A:
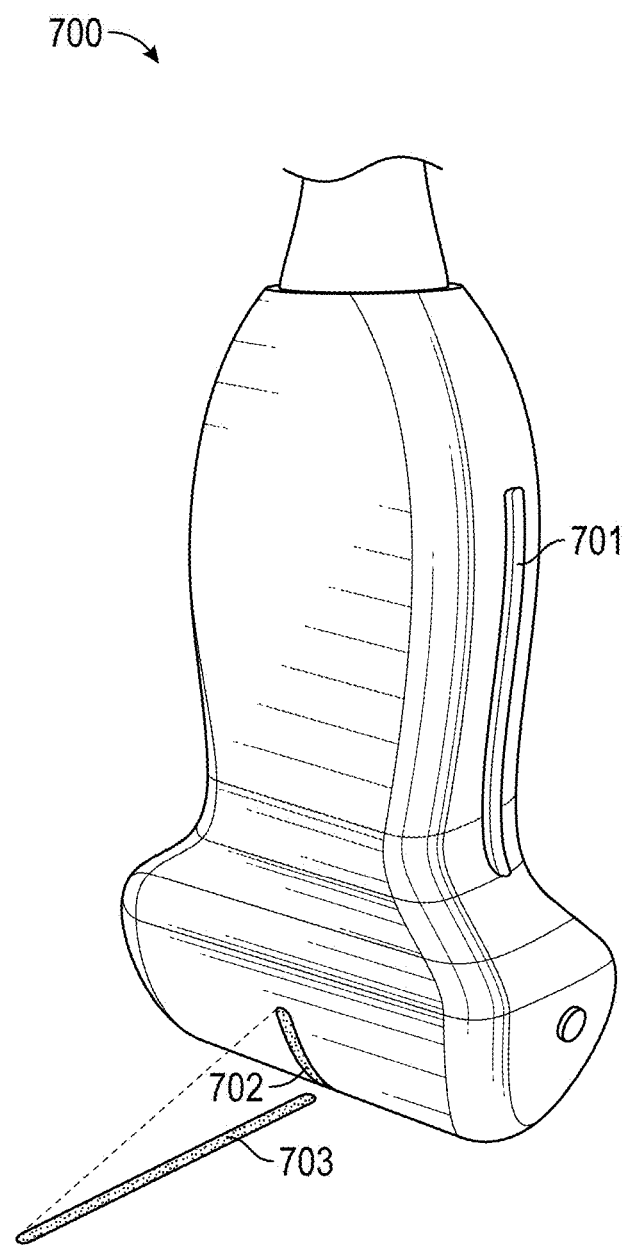
FIG. 7A is a view illustrating an ultrasound scanner according to some embodiments.
Figure 7B:
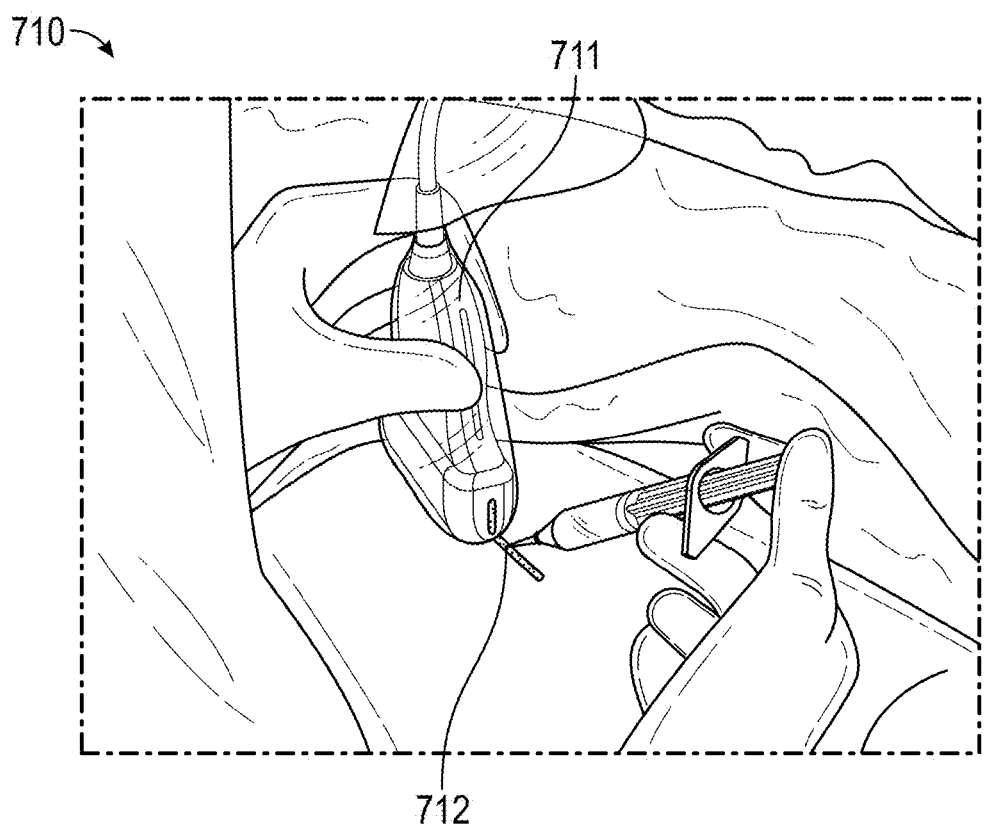
FIG. 7B is a view illustrating a line with a needle insertion point projected with light from an ultrasound scanner according to some embodiments.

FIG. 7A is a view 700 illustrating an ultrasound scanner 701 according to some embodiments. As shown in FIG. 7A, the ultrasound scanner 701 includes a light source that generates light 702 that can be projected as a line 703 onto a patient to aid an ultrasound examination or an ultrasound-guided examination. FIG. 7B is a view 710 illustrating a line with a needle insertion point 712 projected with light (e.g., the light 702) from an ultrasound scanner 711 according to some embodiments. The ultrasound scanner 711 is an example of the ultrasound scanner 701. To project the light, the ultrasound scanner can include a beamformer to beamform light from LEDs of the display interface, light from a MEMS device (e.g., MEMS laser), and/or light from a mini projector, and project the beamformed light onto a patient's skin. Additionally or alternatively, the scanner can include a MEMS laser to project the light. The light can indicate an insertion point for an interventional instrument, such as a needle. The insertion point can be projected together with a line, and the insertion point can be indicated on the line. The light can also project a shape of the patient's blood vessel. For example, the ultrasound scanner can include a neural network to identify arteries, veins, and nerves, and determine a suitable vein for needle insertion (e.g., based on depth, diameter, elasticity, and the like). The neural network can also determine a suitable path for the needle insertion, and project any suitable pattern on the patient's skin, including the shape of the vein, a line, an indicator of the angle of insertion, etc.

Display Data

Display data (e.g., a visual representation, text, etc.) displayed on the display interface of the scanner can include any suitable information. In one example, the visual representation includes data indicating a protocol and/or wireless communication link to use for the pairing. For instance, the visual representation can indicate a bandwidth, carrier frequency, number of carrier frequencies, spacing of carrier frequencies, signal constellation (e.g., 4-QAM, 16-QAM, etc.), a type of error correcting code, a protocol name (e.g., 802.11b, 802.11g, etc.), combinations thereof, and the like. Based on the data included in the visual representation, the display device can initiate the pairing with the scanner, as described above.

Additionally or alternatively, the visual representation can include data regarding the scanner, such as a device ID for the scanner, a type of transducer array included in the scanner, such as linear, planar, phased, curved, etc., an ultrasound center frequency or range of frequencies for the scanner, a cleaning status of the scanner, etc. Based on the data for the scanner that is indicated in the visual representation, the display device can initiate the pairing. In an example, based on the data that is indicated in the visual representation, the display device can configure parameters for an ultrasound examination, such as by setting a depth, gain, beam angle, preset configuration (e.g., cardiac, lung, bladder, etc.), and the like, such as based on the type of transducer included in the scanner (e.g., linear, planar, phased, curved, etc.) and indicated by the visual representation.

Examples of data that the scanner can display on the display interface include:

A state of the scanner, such as, for example, but not limited to, a power mode, an imaging state, a state of a state machine that governs operation of the scanner, etc.

A battery indicator, such as, for example, but not limited to, an amount of battery charge remaining, an amount of charge used, an amount of time remaining for operating the scanner based on battery amount, etc.

An ultrasound image, such as, for example, but not limited to, a lower-resolution version of an ultrasound image displayed on the display device. The display device can communicate the image back to the scanner, or the scanner can generate the lower-resolution image.

A temperature of the scanner. For instance, the scanner can include a temperature sensor that determines a temperature of the scanner, and display the temperature.

A heat map that indicates temperatures across an area of the scanner.

An amount of power/energy of the radiated ultrasound.

A signal strength of a wireless connection between scanner and display device.

An ID of removable transducer array/head.

An indicator of when data is transferred to a display device.

An indicator of a type of data, e.g., image data vs. Biometric data, transferred to a display device.

An authentication status of the user of the scanner. For instance, the scanner can include a camera/eye reader, etc., to authenticate operator, display authentication status and employee ID, number, name, and the like.

A list of display devices connected to (e.g., paired with) the scanner.

A recommendation, such as a type, length, size, etc. of an interventional instrument, as determined by a neural network implemented on the display device, server, and/or scanner.

An alert when the scanner is out of range of the paired display device.

An identification of the paired display device, e.g., device name, device number, etc.

An illumination of the direction and/or desired insertion point of a needle on the patient skin for vascular access. The scanner and/or display device can include a MEMS laser to cast a marker on a patient's skin. In one example, the LEDs are beamformed in a direction of the patient's skin to cast a marker for an insertion point. For example, the LEDs form a phased array.

A status of firmware updates, including a firmware revision number.

A unique pattern for each display device to enable quick pairing with the display device.

A directional indicator of closest charging base or display device. The directional indicator can be updated as the scanner is moved. In an example, a user can speak, such as "Take me to my display device", to initiate the display of the directional indicator(s).

A unique marker that can be camera read to determine a position and orientation of the scanner. In an example, there are multiple scanners in operation simultaneously that can be tracked by a registration system, as previously described. Hence, guidance from a remote operator can be communicated to the sonographer based on tracking the marker(s) displayed by the scanner's display interface. Unique markers are an advantage, since it allows simultaneous tracking of multiple scanners.

An icon in an augmented reality (AR) or virtual reality (VR) environment for remote operation, such as an icon of a patient, a clinician, a scanner, an interventional instrument, a light source (e.g., for photo acoustic imaging), and the like.

In one example, the display interface of the scanner displays guidance information to assist a user during an ultrasound examination. For instance, the display device paired with the scanner can include a neural network trained in any suitable way, such as to recognize anatomy in ultrasound images. The display device can generate a guidance instruction based on an output of the neural network, communicate the guidance instruction to the scanner, and the scanner can display the guidance instruction on the display interface of the scanner. The guidance information displayed by the scanner can include any suitable indicator, such as an arrow to indicate a direction to move the scanner, an arrow or pattern to indicate how to rotate or tilt the scanner, etc.

In an example, the scanner is configured to run a calibration routine to determine a health or fault status of the scanner, and display results of the calibration routine on the display interface of the scanner. For instance, the scanner can run a calibration routine to determine faulty transducer elements of the scanner, as described in U.S. patent application Ser. No. 16/132,262 that has issued as U.S. Pat. No. 11,372,093. Based on results returned by the calibration routine, the scanner can display in the display interface indicators of transducer elements determined to be faulty, such as a number (amount) of faulty transducer elements, a number (amount) of healthy (e.g., not faulty) transducer elements, identification indicators of faulty transducer elements (e.g., the element number or position in the transducer array), etc. In one example, the scanner must have no more than a threshold number of faulty transducer elements to permit pairing with the display device.

In one example, the scanner can be used to authenticate a patient. For instance, the scanner can include a reader (e.g., a camera, laser, bar code scanner, etc.) to read the data on a bracelet worn by a patient in a care facility. The bracelet can include the patient's name, identification number within the care facility, and the like, and the scanner can read this data and display it on the display interface of the scanner prior to performing an ultrasound examination. Additionally or alternatively, the scanner can communicate the patient data to a display device paired with the scanner, and the display device can display the patient data. Hence, the scanner can be used to authenticate the patient to make sure that the correct patient is receiving the examination. In an example, the scanner reads the patient data (e.g., on a patient-worn bracelet or wrist band) with the transducer array of the scanner. For instance, the wrist band can store the data in a format that is readable via ultrasound, such as with a wire matrix, ink doped with particles that are ultrasound readable, etc. Additionally or alternatively, the scan can read the patient data with a light source on the scanner, such as a MEMS laser. In the care facility of the future, the display device can take the form of a heads-up display, goggles, glasses, etc., rather than a smart phone or tablet. Hence, the ability to authenticate the patient via the scanner, without the need for a smart phone or tablet, is an advantage. In some embodiments, the ultrasound scanner is a single-use scanner designed for a specific type of examination, such as for lung examinations, and the display screen of the ultrasound scanner can display information for the type of use. In some other embodiments, the ultrasound scanner is a multi-use scanner.

Figure 8A:
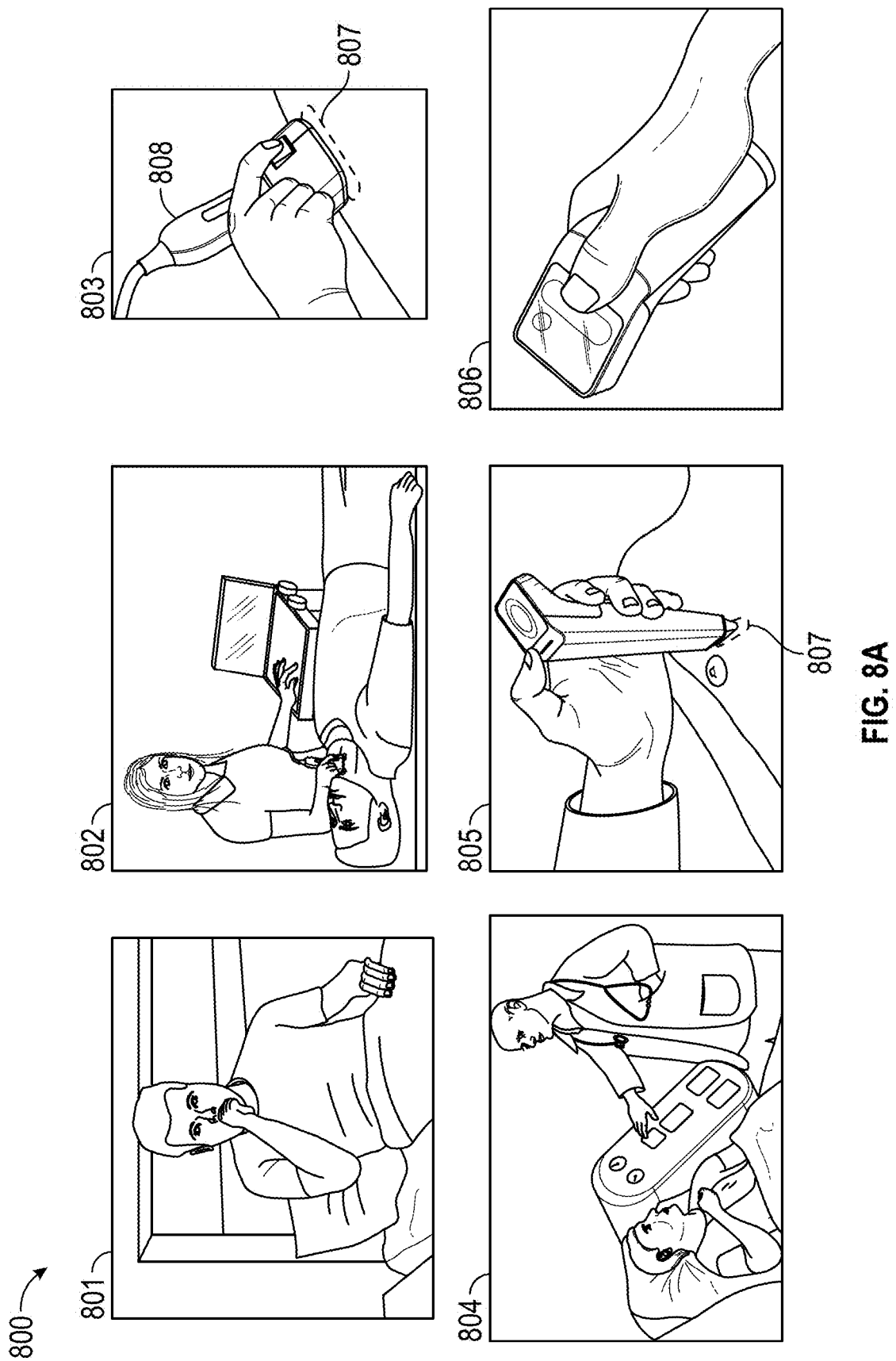
FIG. 8A is a view illustrating a workflow for an ultrasound scanner for lung examinations according to some embodiments.

FIG. 8A is a view 800 illustrating a workflow for an ultrasound scanner for lung examinations according to some embodiments. In block 801, a patient is coughing and feeling shortness of breath. A trained ultrasound operator examines the patient in the block 802. In block 803, the trained operator scans the patient using an ultrasound scanner 808 and marks down a monitoring spot 807 on the patient. In some embodiments, ultrasound scanner 808 is a single-use ultrasound scanner designed for a specific type of examination, such as for lung examinations, and the display screen of the ultrasound scanner can display information for the type of use. In some embodiments, ultrasound scanner 808 is a multi-use ultrasound scanner. The monitoring spot 807 can be generated using light projected by ultrasound scanner 808 onto a patient. The monitoring spot 807 indicates a location on the patient to place the ultrasound scanner for the lung examination.

In the block 804, a non-trained ultrasound operator visits the patient, such as a nurse who is not a credentialed sonographer. In the block 805, the nurse places the ultrasound probe on monitoring spot 807 that was designated by the trained ultrasound operator and activates the ultrasound probe. The ultrasound probe can include a neural network, or be paired with a display device that includes a neural network. The neural network can process the ultrasound data from the scanner and display information relevant to the ultrasound examination, such as "5", the number of A lines or B lines to determine that fluid is not accumulated in the lung. Hence, a pass/fail criteria can be tested without ever displaying an ultrasound image, and the follow-up examination can be performed by the nurse (e.g., non-trained ultrasound operator), as opposed to a trained and credentialed sonographer. In the block 806, the non-trained ultrasound operator uploads the data for review by a doctor.

Figure 8B:
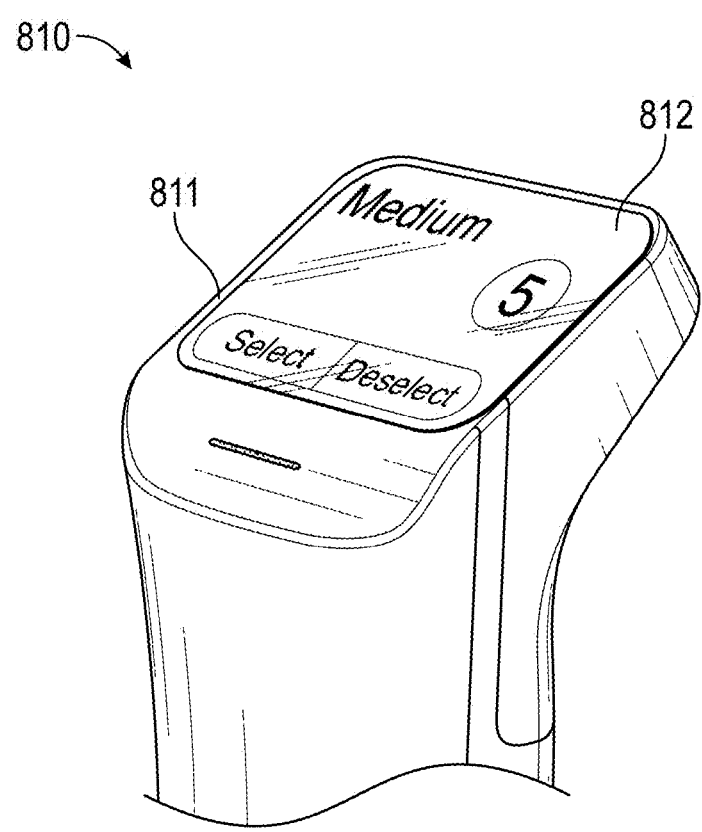
FIG. 8B is a view illustrating a single-use scanner with a display screen according to some embodiments.
Figure 9:
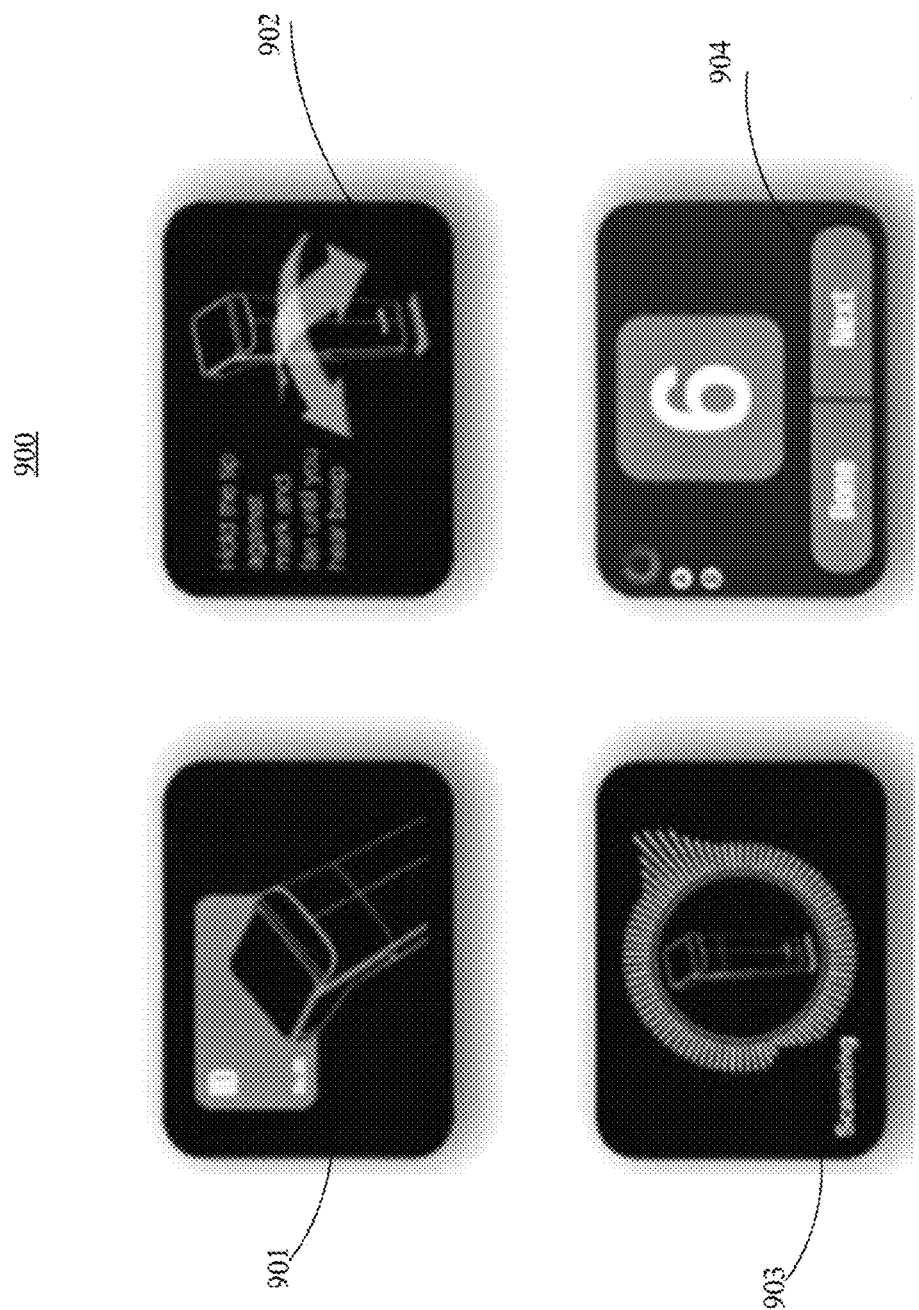
FIG. 9 is a view illustrating examples of data that can be displayed on a display screen of a single-use scanner in the absence of a trained sonographer according to some embodiments.

FIG. 8B is a view 810 illustrating a single-use scanner 811 with a display screen 812 according to some embodiments. The scanner 811 is an example of the scanner 808 in FIG. 8A. FIG. 9 is a view 900 illustrating examples of data that can be displayed on a display screen 812 of a single-use scanner 811 in the absence of a trained sonographer according to some embodiments. As shown in FIG. 9, the display screen can display a visual representation 901 representing identification data. The display screen can display a visual representation 902 representing instructions to an operator for how to move the ultrasound scanner. For example, visual representation 902 can include instructions "hold the tip against mark and fan until you hear beep", or other instructions to an operator. The display screen can display a visual representation 903 that indicates an operating mode of the scanner (e.g., "scanning", "updating" (such as when receiving software/firmware updates), "charging", "pairing", etc.). The display screen can display a visual representation 904 that represent data that are relevant to an ultrasound examination, e.g., the number of A lines or B lines to determine that fluid is not accumulated in the lung, buttons indicating that the procedure is "done" or "next" operation needs to be performed (e.g., a next step in an ultrasound examination protocol), scanning mode icon, and the like.

Figure 10:
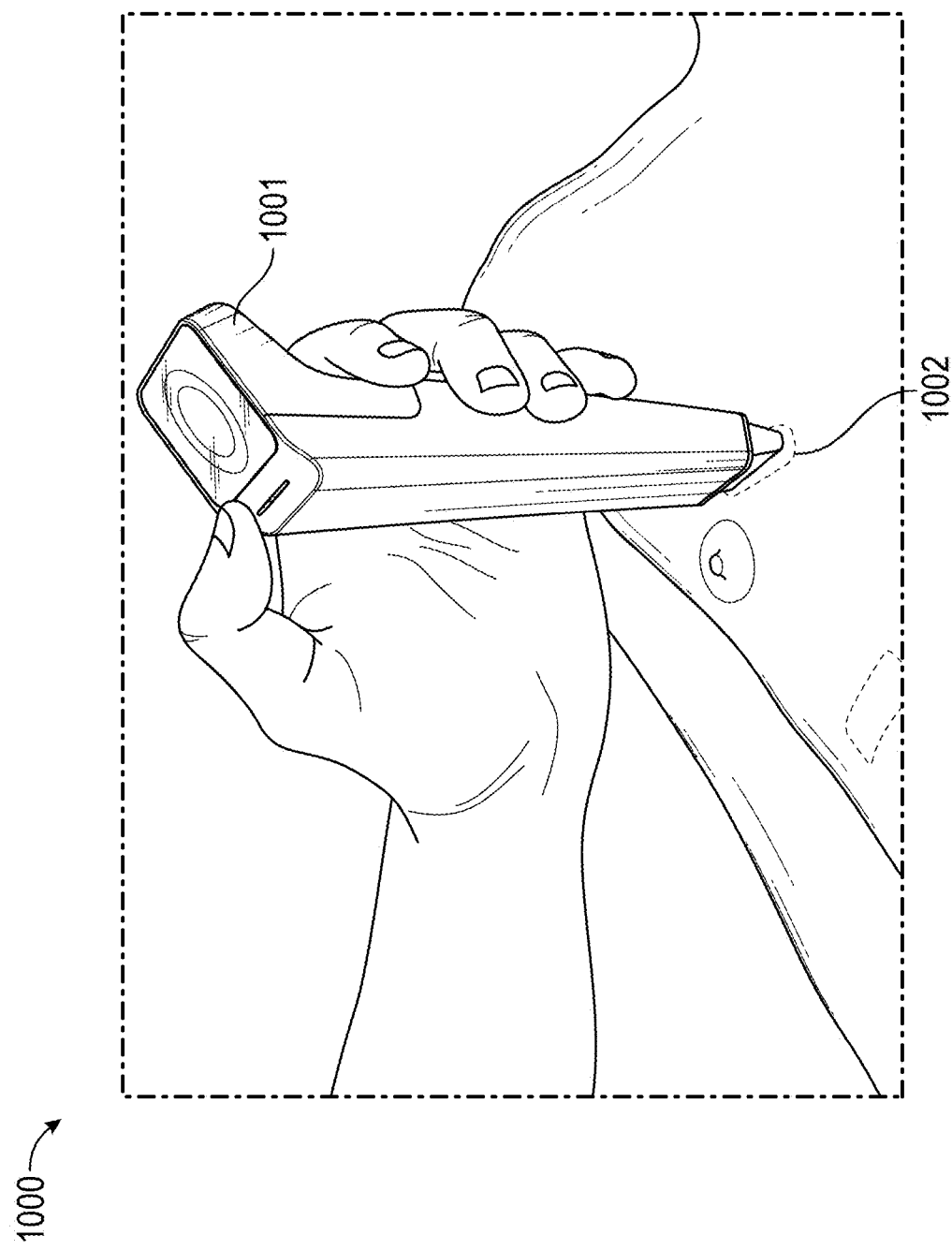
FIG. 10 is a view illustrating use of a single-use scanner with patient markers according to some embodiments.

FIG. 10 is a view 1000 illustrating use of a single-use scanner 1001 with patient markers 1002 according to some embodiments. The single-use scanner 1001 is an example of the scanner 811. As shown in FIG. 10, an operator places a single-use scanner 1001 on a patient at marker locations 1002 designated by a trained sonographer based on the light projected by at least one light source of the ultrasound scanner, as described above.

Figure 11:
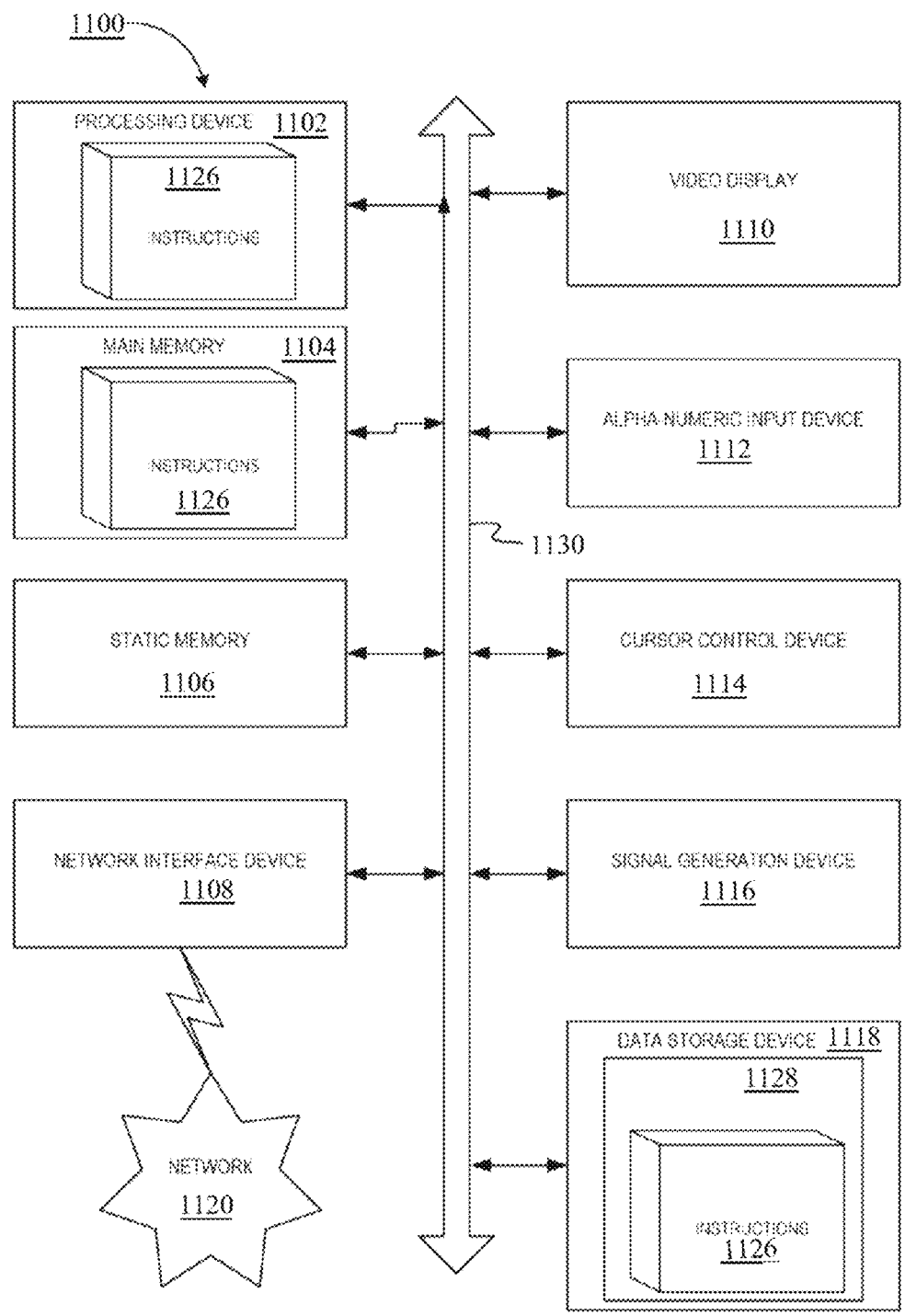
FIG. 11 is a block diagram of an example computing device that can perform one or more of the operations described herein, in accordance with some embodiments.

FIG. 11 is a block diagram of an example computing device 1100 that may perform one or more of the operations described herein, in accordance with some embodiments. Computing device 1100 can be connected to other computing devices in a LAN, an intranet, an extranet, and/or the Internet. The computing device can operate in the capacity of a server machine in client-server network environment or in the capacity of a client in a peer-to-peer network environment. The computing device can be provided by a personal computer (PC), a server computing, a desktop computer, a laptop computer, a tablet computer, a smartphone, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein. In some embodiments, the computing device 1100 can be one or more of an access point and a packet forwarding component.

The example computing device 1100 includes a processing device (e.g., a general purpose processor, a PLD, etc.) 1102, a main memory 1104 (e.g., synchronous dynamic random access memory (DRAM), read-only memory (ROM)), a static memory 1106 (e.g., flash memory and a data storage device 1118), which can communicate with each other via a bus 1130.

Processing device 1102 can be provided by one or more general-purpose processing devices such as a microprocessor, central processing unit, or the like. In an illustrative example, processing device 1102 comprises a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 1102 can also comprise one or more special-purpose processing devices such as an application specific integrated circuit (ASIC), a field programmable gate array (FPGA), a digital signal processor (DSP), network processor, or the like. The processing device 1102 can be configured to execute the operations described herein, in accordance with one or more aspects of the present disclosure, for performing the operations and steps discussed herein.

Computing device 1100 includes a network interface device 1108 which can communicate with a network 1120. The computing device 1100 also includes a video display unit 1110 (e.g., a liquid crystal display (LCD) or a cathode ray tube (CRT)), an alphanumeric input device 1112 (e.g., a keyboard), a cursor control device 1114 (e.g., a mouse) and an acoustic signal generation device 1116 (e.g., a speaker, and/or a microphone). In one embodiment, video display unit 1110, alphanumeric input device 1112, and cursor control device 1114 can be combined into a single component or device (e.g., an LCD touch screen).

Data storage device 1118 includes a computer-readable storage medium 1128 on which is stored one or more sets of instructions 1126, e.g., instructions for carrying out the operations described herein, in accordance with one or more aspects of the present disclosure. Instructions 1126 can also reside, completely or at least partially, within main memory 1104 and/or within processing device 1102 during execution thereof by computing device 1100, main memory 1104 and processing device 1102 also constituting computer-readable media. The instructions may further be transmitted or received over a network 1120 via network interface device 1108.

While computer-readable storage medium 1128 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

It is apparent from this description that embodiments described herein may be embodied, at least in part, in software. That is, the techniques and methods may be carried out in a data processing system or set of data processing systems in response to one or more processors executing a sequence of instructions stored in a storage medium, such as a non-transitory machine-readable storage media, such as volatile DRAM or nonvolatile flash memory. In various embodiments, hardwired circuitry may be used in combination with software instructions to implement the embodiments described herein. Thus, the techniques and methods are not limited to any specific combination of hardware circuitry and software, or to any particular source for the instructions executed by the one or more data processing systems.

Unless specifically stated otherwise, terms such as "transmitting," "determining," "receiving," "generating," "or the like, refer to actions and processes performed or implemented by computing devices that manipulates and transforms data represented as physical (electronic) quantities within the computing device's registers and memories into other data similarly represented as physical quantities within the computing device memories or registers or other such information storage, transmission or display devices. Also, the terms "first," "second," "third," "fourth," etc., as used herein are meant as labels to distinguish among different elements and may not necessarily have an ordinal meaning according to their numerical designation.

Examples described herein also relate to an apparatus for performing the operations described herein. This apparatus may be specially constructed for the required purposes, or it may comprise a general purpose computing device selectively programmed by a computer program stored in the computing device. Such a computer program may be stored in a computer-readable non-transitory storage medium.

The methods and illustrative examples described herein are not inherently related to any particular computer or other apparatus. Various general purpose systems may be used in accordance with the teachings described herein, or it may prove convenient to construct more specialized apparatus to perform the required method steps. The required structure for a variety of these systems will appear as set forth in the description above.

The above description is intended to be illustrative, and not restrictive. Although the present disclosure has been described with references to specific illustrative examples, it will be recognized that the present disclosure is not limited to the examples described. The scope of the disclosure should be determined with reference to the following claims, along with the full scope of equivalents to which the claims are entitled.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although the method operations were described in a specific order, it should be understood that other operations may be performed in between described operations, described operations may be adjusted so that they occur at slightly different times or the described operations may be distributed in a system which allows the occurrence of the processing operations at various intervals associated with the processing.

Various units, circuits, or other components may be described or claimed as "configured to" or "configurable to" perform a task or tasks. In such contexts, the phrase "configured to" or "configurable to" is used to connote structure by indicating that the units/circuits/components include structure (e.g., circuitry) that performs the task or tasks during operation. As such, the unit/circuit/component can be said to be configured to perform the task, or configurable to perform the task, even when the specified unit/circuit/component is not currently operational (e.g., is not on). The units/circuits/components used with the "configured to" or "configurable to" language include hardware—for example, circuits, memory storing program instructions executable to implement the operation, etc. Reciting that a unit/circuit/component is "configured to" perform one or more tasks, or is "configurable to" perform one or more tasks, is expressly intended not to invoke 35 U.S.C. 112, sixth paragraph, for that unit/circuit/component. Additionally, "configured to" or "configurable to" can include generic structure (e.g., generic circuitry) that is manipulated by software and/or firmware (e.g., an FPGA or a general-purpose processor executing software) to operate in manner that is capable of performing the task(s) at issue. "Configured to" may also include adapting a manufacturing process (e.g., a semiconductor fabrication facility) to fabricate devices (e.g., integrated circuits) that are adapted to implement or perform one or more tasks. "Configurable to" is expressly intended not to apply to blank media, an unprogrammed processor or unprogrammed generic computer, or an unprogrammed programmable logic device, programmable gate array, or other unprogrammed device, unless accompanied by programmed media that confers the ability to the unprogrammed device to be configured to perform the disclosed function(s).

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the invention is not to be limited to the details given herein, but may be modified within the scope and equivalents of the appended claims.

What is claimed is:

1. An ultrasound system comprising:
a display device; and
an ultrasound probe having an interface configured to display a visual representation comprising a first light representing first data to initiate pairing with the display device that is separate from the ultrasound probe, and a first transceiver comprising a first processing circuitry that is configured to communicate over a communication link with the display device,
the display device having a reader that includes one or more sensors configured to sense the first light of the visual representation displayed by the ultrasound probe and a decoder configured to decode the first data from the first light, and a second transceiver comprising a second processing circuitry that is configured to initiate communication with the first processing circuitry to pair the ultrasound probe and the display device over the communication link based on the first data.

2. The ultrasound system as described in claim 1, wherein the first light includes at least one of a quick response (QR) code, a bar code, an animation sequence, a pattern, and an image.

3. The ultrasound system as described in claim 1, wherein the interface is sealed from an environment outside the ultrasound probe.

4. The ultrasound system as described in claim 3, wherein the interface includes an array of light emitting diodes (LEDs) that are visibly hidden from the environment when the LEDs are inactive.

5. The ultrasound system as described in claim 1, wherein the ultrasound probe is a first ultrasound probe that is implemented to communicate with an additional ultrasound probe over an additional communication link to indicate that the first ultrasound probe is in said communication with the display device and is not available for pairing with the additional ultrasound probe.

6. The ultrasound system as described in claim 1, wherein the ultrasound probe includes a light source configured to project a second light onto a patient to indicate an insertion point for an interventional instrument.

7. The ultrasound system as described in claim 6, wherein the light source is configured to project the second light onto the patient to indicate a shape of a blood vessel.

8. The ultrasound system as described in claim 6, wherein the light source includes at least one of light emitting diodes (LEDs) of the display, a mini projector, and a MEMS device, and the light source is implemented to generate the second light with the at least one of the LEDs, the mini projector, and the MEMS device.

9. The ultrasound system as described in claim 1, wherein the ultrasound probe includes:
- a transducer system implemented to generate ultrasound data based on reflections of ultrasound signals transmitted by the transducer system at a patient-worn identifier; and
- a processor implemented to determine patient identification data based on the ultrasound data;
- wherein at least one of the interface and the display device is implemented to display the patient identification data.

10. The ultrasound system as described in claim 1, wherein the ultrasound probe is configured to obtain an instruction to move the ultrasound probe, and the interface is configured to display an additional visual representation that indicates how to move the ultrasound probe based on the instruction.

11. The ultrasound system as described in claim 1, wherein the ultrasound probe is configured to receive a removable head having a transducer array, and the interface is configured to display an identifier of the removable head.

12. The ultrasound system as described in claim 11, wherein identifier indicates the transducer array as one of linear, planar, phased, and curved.

13. An ultrasound system comprising:
- a display device; and
- an ultrasound probe having at least one light source configured to emit a first light and a processor configured to encode first data into the first light to initiate pairing with the display device that is separate from the ultrasound probe, the
- display device having a receiver including one or more sensors configured to sense the first light and a decoder configured to decode the first data from the first light, wherein:
- the ultrasound probe includes a first transceiver comprising a first processing circuitry that is configured to communicate over a communication link;
- the display device includes a second transceiver comprising a second processing circuitry that is configured to communicate over the communication link; and
- the second processing circuitry is implemented to, based on the first data decoded from the first light, initiate communication with the first processing circuitry to pair the ultrasound probe and the display device over the communication link.

14. The ultrasound system as described in claim 13, wherein the processor is implemented to encode the data into the first light by modulating at least one of a frequency of the first light, a phase of the first light, an amplitude of the first light, and a polarization of the first light.

15. The ultrasound system as described in claim 13, wherein the at least one light source includes multiple light sources, and the processor is implemented to encode the data into the first light based on locations of the multiple light sources on the ultrasound probe.

16. The ultrasound system as described in claim 13, wherein the light includes visible light having a wavelength between 380 nanometers and 740 nanometers.

17. The ultrasound system as described in claim 13, wherein the at least one light source includes multiple light sources, and further comprising a registration system including:
- one or more light sensors implemented to sense the first light emitted from the multiple light sources; and
- a processor system implemented to determine an orientation of the ultrasound probe based on the first light sensed by the one or more light sensors.

18. The ultrasound system as described in claim 13, wherein the data indicates at least one of an availability, a battery status, a cleanliness status, and a transducer configuration of the ultrasound probe.

19. An ultrasound probe comprising:
- a display interface including an array of light emitting diodes (LEDs) configured to emit a first light pattern to sense by one or more sensors of a display device that is separate from the ultrasound probe, the first light pattern representing first data to initiate pairing with the display device over a communication link, wherein the LEDs are visibly hidden from an environment outside the ultrasound probe when the LEDs are inactive, the display interface being sealed from the environment; and
- a first transceiver coupled to the display interface, the first transceiver comprising a first processing circuitry that is configured to communicate with the display device over the communication link, the display device comprising the one or more sensors configured to sense the first light pattern and a second processing circuitry coupled to the one or more sensors, wherein the first processing circuitry is configured to receive a communication from the second processing circuitry over the communication link to pair the ultrasound scanner and the display device in response to the one or more sensors sensing the first light pattern indicating the first data.

* * * * *